United States Patent
Chasin et al.

(10) Patent No.: US 6,319,928 B1
(45) Date of Patent: Nov. 20, 2001

(54) PURINE DERIVATIVES HAVING PHOSPHODIESTERASE IV INHIBITION ACTIVITY

(75) Inventors: Mark Chasin, Manalapan, NJ (US); David J. Cavalla, Cambridge (GB); Peter Hofer, Liestal (CH); Peter Wintergerst; Andre Gehrig, both of Basel (CH)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/418,331

(22) Filed: Oct. 14, 1999

Related U.S. Application Data

(62) Continuation of application No. 09/285,473, filed on Apr. 2, 1999, which is a continuation-in-part of application No. 08/578,580, filed as application No. PCT/GB94/01334 on Jun. 21, 1994, now Pat. No. 5,939,422, application No. 09/418,331, which is a continuation-in-part of application No. 09/200,615, filed on Nov. 30, 1998, now abandoned, and a continuation-in-part of application No. 09/210,556, filed on Dec. 11, 1998, now Pat. No. 6,228,859.

(51) Int. Cl.$^7$ .................. C07D 473/18; C07D 473/24; A61K 31/522; A61K 31/52; A61P 11/06

(52) U.S. Cl. ............................... 514/262; 544/276

(58) Field of Search ............... 514/262; 544/276

(56) References Cited

U.S. PATENT DOCUMENTS

| | | | |
|---|---|---|---|
| 2,691,654 | 10/1954 | Hitchings | 260/247.5 |
| 2,697,709 | 12/1954 | Hitchings et al. | 260/252 |
| 2,844,577 | 7/1958 | Acker | 260/254 |
| 2,903,455 | 9/1959 | Strong | 260/252 |
| 2,956,998 | 10/1960 | Baizer | 260/252 |

(List continued on next page.)

FOREIGN PATENT DOCUMENTS

| | | |
|---|---|---|
| 0203721 | 12/1986 | (EP) . |
| 256692 | 2/1988 | (EP) . |
| 0675124 | 10/1995 | (EP) . |
| 0728759 | 8/1996 | (EP) . |
| 1548252 | 10/1968 | (FR) . |
| 1077689 | 8/1967 | (GB) . |
| 2041359 | 9/1980 | (GB) . |
| 2120665 | 12/1993 | (GB) . |

(List continued on next page.)

OTHER PUBLICATIONS

Stafford and Feldman, "Annual Reports in Medicinal Chemistry", Academic Press, San Diego, 1996, Chapt. 8, p76–78.*
Gertrude Elion, JOC, 27, 1962, 2478–2491.*
Bergmann & Tamari, J. Chem. Soc., 1961, 4468–4472.*
Shimada, Junichi; Kuroda, Takeshi; Suzuki, Fumio, J. Heterocycl. Chem., 30(1), 241–6 (English) 1993.*
Buell, J. Biol. Chem., 72, 1927, 745.*
Suzuki, Fumio; Shimada, Junichi; Nonaka, Hiromi; Ishi, Akio; Shiozaki, Shizuo; Ichikawa, Shunji; Ono, Eikichi, J. Med. Chem., 35(19), 3578–81 (English) 1992.*
Moharram; Hussieny H.; Mansour, S. A.; Osman, A. N., Egypt. J. Pharm. Sci., 31(1–4), 487–94 (English) 1990.*
Kazimierczuk; Z.; Shugar, D. Acta Biochim. Pol., 21(4), 455–63 (English) 1974.*
J. A. Montgomery et al, JACS, 81, 1959, 3963–3967.*
Robins, JACS, 74, 1952, 3624–.*
Gutorov, L. A.; Golovchinskaya, E. S., Khim–Farm. Zh. (1969), 3(7),4–10.*

Primary Examiner—Mukund J. Shah
Assistant Examiner—Thomas McKenzie
(74) Attorney, Agent, or Firm—Davidson, Davidson & Kappel, LLC

(57) ABSTRACT

A compound of the formula:

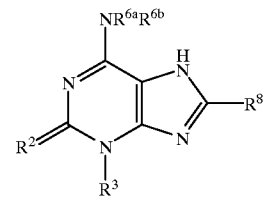

wherein $R_2$ is O or S;

$R_3$, $R_{6a}$ and $R_8$ are the same or different and each represent a $C_{1-8}$ alkyl which is unbranched or branched and unsubstituted or substituted with OH, alkoxy, $CO_2H$, =NOH, =NOCONH$_2$, or =O; $C_{3-8}$ cycloalkyl which is unsubstituted or substituted with OH, alkoxy, $CO_2H$, =NOH, =NOCONH$_2$, or =O; $C_{4-8}$ cycloalkylalkyl wherein the cycloalkyl portion is unsubstituted or substituted with OH, alkoxy, $CO_2H$, =NOH, =NOCONH$_2$, or =O; aryl which is unsubstituted or substituted with Cl, $NH_2$, alkylamino, dialkylamino, amido, $C_1$–$C_8$ alkylamido, $C_1$–$C_3$ dialkylamido, OH, alkoxy, HC=NOH, HC=NOCONH$_2$, $C_1$–$C_3$ alkyl, phenyl or benzyl; aralkyl ($C_{1-4}$); heterocyclyl; heterocyclylalkyl ($C_1$–$C_4$); and heteroaryl;

$R_{6b}$ represents a H or $R_{6a}$, or together $R_{6b}$, N, and $R_{6a}$ make a 3 to 8 member ring containing at least one carbon, from one to three nitrogen atoms, from zero to two oxygen atoms, from zero to two sulfur atoms, said ring optionally substituted with alkoxy, $CO_2H$, CONH$_2$, =NOH, =NOCONH$_2$, =O; and where aryl is phenyl or naphthyl, the heterocyclyl is a 5, 6 or 7 membered ring including from one to three nitrogen atoms, and from zero to two oxygen atoms, from zero to two sulfur atoms, and can be substituted as in aryl on the carbons or nitrogens of that ring; or a pharmaceutically acceptable salt thereof, provided that when $R_3$ is propyl, $R_8$ is not cyclopentyl, noradamantyl, or dicyclopropylmethyl.

50 Claims, No Drawings

U.S. PATENT DOCUMENTS

| | | | |
|---|---|---|---|
| 2,957,875 | 10/1960 | Lyttle | 260/252 |
| 2,966,488 | 12/1960 | Shive | 260/252 |
| 3,079,378 | 2/1963 | Schroeder et al. | 260/211.5 |
| 3,135,753 | 6/1964 | Hitchings | 260/252 |
| 3,215,696 | 11/1965 | Denayer | 260/252 |
| 3,225,046 | 12/1965 | Zwahlen | 260/252 |
| 3,669,979 | 6/1972 | Freyermuth | 260/304 |
| 3,952,001 | 4/1976 | Brookes et al. | 260/308 |
| 4,241,063 | 12/1980 | Natio et al. | 424/257 |
| 4,361,699 | 11/1982 | Rasmusson et al. | 544/277 |
| 4,407,802 | 10/1983 | Graham et al. | 424/253 |
| 4,492,592 | 1/1985 | Diaz et al. | 62/18 |
| 4,728,644 | 3/1988 | Yuki et al. | 514/218 |
| 4,883,801 | 11/1989 | Nathanson | 514/263 |
| 4,971,972 | 11/1990 | Doll et al. | 514/265 |
| 4,981,857 | 1/1991 | Daluge et al. | 514/263 |
| 5,057,517 | 10/1991 | Johnston et al. | 514/254 |
| 5,091,431 | 2/1992 | Tulshian et al. | 514/262 |
| 5,110,818 | 5/1992 | Allgeier | 514/262 |
| 5,117,830 | 6/1992 | McAfee | 128/654 |
| 5,177,074 | 1/1993 | Allen et al. | 514/234.2 |
| 5,270,316 | * 12/1993 | Suzuki et al. | 514/267 |
| 5,290,782 | 3/1994 | Suzuki et al. | 514/263 |
| 5,939,422 | 8/1999 | Cavalla et al. | 514/261 |

FOREIGN PATENT DOCUMENTS

| | | |
|---|---|---|
| 7606986 | 1/1976 | (JP) . |
| 5121529 | 2/1976 | (JP) . |
| 7654587 | 5/1976 | (JP) . |
| 0215948 | 10/1989 | (NZ) . |
| 8706576 | 11/1987 | (WO) . |
| 9314081 | 7/1993 | (WO) . |
| 9314082 | 7/1993 | (WO) . |
| 9325517 | 12/1993 | (WO) . |
| 9402465 | 2/1994 | (WO) . |
| 9410118 | 5/1994 | (WO) . |
| 9412461 | 6/1994 | (WO) . |
| 9414742 | 7/1994 | (WO) . |
| 9414800 | 7/1994 | (WO) . |
| 9420446 | 9/1994 | (WO) . |
| 9420455 | 9/1994 | (WO) . |
| 9422859 | 10/1994 | (WO) . |

* cited by examiner

PURINE DERIVATIVES HAVING PHOSPHODIESTERASE IV INHIBITION ACTIVITY

This application is a continuation of U.S. patent application Ser. No. 09/285,473 filed Apr. 2, 1999, which is a continuation-in-part of U.S. patent application Ser. No. 08/578,580, entitled "Novel Chemical Compounds Having PDE IV Inhibition Activity", filed Apr. 8, 1996, now U.S. Pat. No. 5,939,422 which is the National phase filing of International Application No. PCT/GB 94/01334, filed Jun. 21, 1994; and is also a continuation-in-part of U.S. patent application Ser. No. 09/200,615, entitled "Novel Chemical Compounds Having PDE IV Inhibition Activity", filed Nov. 30, 1998, now abandoned and is also a continuation-in-part of U.S. patent application Ser. No. 09/210,556, now U.S. Pat. No. 6,228,859, entitled "Purine Derivatives Having Phosphodiesterase IV Inhibition Activity" filed Dec. 11, 1998; the disclosures of all of these parent applications are hereby incorporated by reference.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The struture-activity relationships (SAR) of isozyme-selective inhibitors has been discussed in detail e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

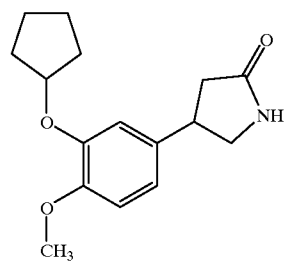

and of RO-20-1724, which has the following structural formula (B):

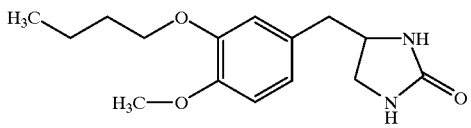

have been studied.

U.S. Pat. No. 4,308,278 discloses compounds of the formula (C)

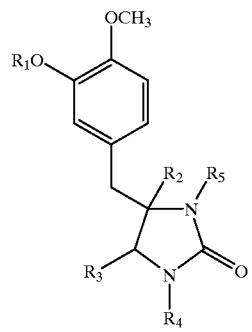

wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

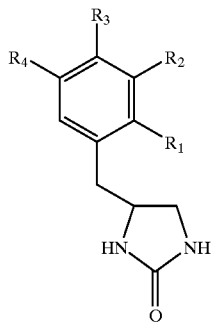

Substituents $R_1$–$R_4$ in Formula D represent a variety of groups, including hydrogen and lower alkyl.

PCT publication WO 87/06576 discloses antidepressants of Formula E:

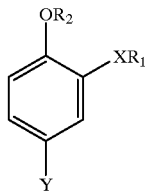

wherein $R_1$ is a polycycloalkyl group having from 7 to 11 carbon atoms; $R_2$ is methyl or ethyl; X is O or NH; and Y comprises a mono-or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

OBJECTS AND SUMMARY OF THE INVENTION

It is accordingly an object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma; allergies; inflammation; depression; dementia, including Alzheimer's disease, vascular dementia, and multi-in-farct dementia; a disease caused by Human Immunodeficiency Virus; and disease states associated with abnormally high physiological levels of inflammatory cytokines.

Other objects and advantages of the present invention will become apparent from the following detailed description thereof. With the above and other objects in view, the present invention comprises compounds having the general formula (I):

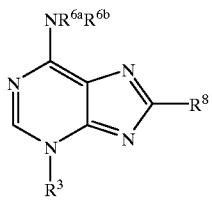

(I)

wherein
R³ is selected from the group consisting of
hydrogen;
$C_{1-10}$ alkyl which is unbranched or branched and is optionally substituted with 1–3 members of the group consisting of OH, $C_{1-10}$ alkoxy, $C_{3-12}$ cycloalkoxy, halogen, =NOH, =NOCONH$_2$, CO$_2$H, =O or benzyloxy, said benzyloxy optionally substituted with 1–3 members of the group consisting of halogen, $C_{1-10}$ alkyl, $C_{3-12}$ cycloalkyl, $C_{1-10}$ alkoxy, $C_{3-12}$ cycloalkoxy;
$C_{2-10}$ alkenyl which is unbranched or branched and is optionally substituted with 1–3 members of the group consisting of OH, $C_{3-12}$ cycloalkyl, $C_{1-10}$ alkoxy, $C_{3-12}$ cycloalkoxy, halogen, =NOH, =NOCONH$_2$, CO$_2$H or =O;
$C_{3-10}$ cycloalkyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
$C_{3-10}$ cycloalkenyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
$C_{3-12}$ cycloalkyl($C_{1-10}$)alkyl wherein the cycloalkyl portion is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
aryl which is optionally substituted with 1–3 members of the group consisting of $C_{1-10}$ alkyl $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl;
ar($C_{1-4}$)alkyl wherein the aryl moiety is optionally substituted with 1–3 members of the group consistng of carboxy, $C_{1-10}$ alkylcarboxy, halogen; hydroxy, hydroxy($C_{1-10}$)alkoxy, nitro, trihalocarbon, benzyloxy, heterocyclyl $C_{1-10}$ cycloalkyl($C_{3-12}$) alkyloxy, ar($C_{1-10}$)alkyloxy, aryloxy, amino($C_{1-10}$) alkoxy, $C_{1-10}$ alkylamino($C_{1-10}$)alkoxy, heteroaryloxy, heteroar($C_{1-10}$)alkyloxy, heterocyclyloxy, $C_{1-10}$ alkyl, $C_{3-12}$ cycloalkyl, $C_{1-10}$ alkoxy or $C_{3-12}$ cycloalkoxy said alkoxy and cycloalkoxy optionally substituted in one position at the alkyl moiety with hydroxy and said heterocyclyl is optionally substituted with $C_{1-10}$ alkyl; and wherein the alkyl moiety of said ar ($C_{1-4}$)alkyl is optionally substituted with OH, halogen, $C_{1-10}$ alkoxy and $C_{3-12}$ cycloalkoxy said alkoxy and cycloalkoxy being optionally substituted in one position at the alkyl moiety with hydroxy;
heterocyclyl which is optionally substituted on the carbons or nitrogens of the ring with 1–3 members of the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl;
heterocyclyl($C_1$-$C_4$)alkyl wherein said heterocyclyl moiety is optionally substituted on the carbons or nitrogens of the ring with 1–3 members of the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl, and wherein said alkyl moiety is optionally substituted with OH, $C_{1-10}$ alkoxy, $C_{3-12}$ cycloalkoxy, $C_{3-12}$ cycloalkyl, halogen or halo($C_{1-10}$)alkyl;
heteroaryl, which is optionally substituted with 1–3 members of the group consisting of $C_{1-10}$ alkyl, $C_{3-12}$ cycloalkyl, halogen, nitro, CF$_3$, $C_{1-10}$ alkoxy, $C_{3-12}$ cycloalkoxy or oxo; and
heteroaryl($C_{1-4}$)alkyl, wherein the heteroaryl moiety is optionally substituted with 1–3 members of the group consisting of $C_{1-10}$ alkyl, $C_{3-12}$ cycloalkyl, halogen, nitro, trihalocarbon, $C_{1-10}$ alkoxy or $C_{3-12}$ cycloalkoxy;
R⁸ is selected from the group consisting of
hydrogen;
$C_{1-10}$ alkyl which is unbranched or branched and is optionally substituted with 1–3 members of the group consisting of OH, $C_{1-10}$ alkoxy, $C_{3-12}$ cycloalkoxy, halogen, =NOH, =NOCONH$_2$, CO$_2$H, =O or benzyloxy, said benzyloxy optionally substituted with 1–3 members of the group consisting of halogen, $C_{1-10}$ alkyl, $C_{3-12}$ cycloalkyl, $C_{1-10}$ alkoxy, $C_{3-12}$ cycloalkoxy;
$C_{2-10}$ alkenyl which is unbranched or branched and is optionally substituted with 1–3 members of the group consisting of OH, $C_{3-12}$ cycloalkyl, $C_{1-10}$ alkoxy, $C_{3-12}$ cycloalkoxy, halogen, =NOH, =NOCONH$_2$, CO$_2$H or =O;
$C_{3-10}$ cycloalkyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
$C_{3-10}$ cycloalkenyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
$C_{3-12}$ cycloalkyl($C_{1-10}$)alkyl wherein the cycloalkyl portion is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;
aryl which is optionally substituted with 1–3 members of the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl;

ar($C_{1-4}$)alkyl wherein the aryl moiety is optionally substituted with 1–3 members of the group consisting of carboxy, $C_{1-10}$, alkylcarboxy, halogen, hydoxy, hydroxy($C_{1-10}$)alkoxy, nitro, trihalocarbon, benzyloxy, heterocyclyl, $C_{1-10}$ cycloalkyl($C_{3-12}$) alkyloxy, ar($C_{1-10}$)alkyloxy, aryloxy, amino($C_{1-10}$) alkoxy, $C_{1-10}$ alkylamino($C_{1-10}$)alkoxy, heteroaryloxy, heteroar($C_{1-10}$)alkyloxy, heterocyclyloxy, $C_{1-10}$ alkyl, $C_{3-12}$ cycloalkyl, $C_{1-10}$ alkoxy or $C_{3-12}$ cycloalkoxy said alkoxy and cycloalkoxy optionally suibstituted in one position at the alkyl moiety with hydroxy and said heterocyclyl is optionally substituted with $C_{1-10}$ alkyl; and wherein the alkyl moiety of said ar ($C_{1-4}$)alkyl is optionally substituted with OH, halogen, $C_{1-10}$ alkoxy and $C_{3-12}$ cycloalkoxy said alkoxy and cycloalkoxy being optionally substituted in one position at the alkyl moiety with hydroxy;

heterocyclyl which is optionally substituted on the carbons or nitrogens of the ring with 1–3 members of the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsufonylamino, C=NOH, C=NOCONH$_2$, phenyl or benzyl;

heterocyclyl($C_1$–$C_4$)alkyl wherein said heterocyclyl moiety is optionally substituted on the carbons or nitrogens of the ring with 1–3 members of the group consistng of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl, and wherein said alkyl moiety is optionally substituted with OH, $C_{1-10}$ alkoxy, $C_{3-12}$ cycloalkoxy, $C_{3-12}$ cycloalkyl, halogen or halo($C_{1-10}$)alkyl;

heteroaryl, which is optionally substituted with 1–3 members of the group consisting of $C_{1-10}$ alkyl, $C_{3-12}$ cycloalkyl, halogen, nitro, CF$_3$, $C_{1-10}$ alkoxy, $C_{3-12}$ cycloalkoxy or oxo; and heteroaryl($C_{1-4}$)alkyl, wherein the heteroaryl moiety is optionally substituted with 1–3 members of the group consisting of $C_{1-10}$ alkyl, $C_{3-12}$ cycloalky, halogen, nitro, trihalocarbon, $C_{1-10}$ alkoxy or $C_{3-12}$ cycloalkoxy;

$R^{6a}$ and $R^{6b}$ are independendy selected from the group consisting of hydrogen;

$C_{1-10}$ alkyl which is unbranched or branched and is optionally substituted with 1–3 members of the group consisting of OH, $C_{1-10}$ alkoxy, $C_{3-12}$ cycloalkoxy, halogen, =NOH, =NOCONH$_2$, CO$_2$H, =O or benzyloxy, said benzyloxy optionally substituted with 1–3 members of the group consisting of halogen, $C_{1-10}$ alkyl, $C_{3-12}$ cycloalkyl, $C_{1-10}$ alkoxy, $C_{3-12}$ cycloalkoxy;

$C_{2-10}$ alkenyl which is unbranched or branched and is optionally substituted with 1–3 members of the group consisting of OH, $C_{3-12}$ cycloalkyl, $C_{1-10}$ alkoxy, $C_{3-12}$ cycloalkoxy, halogen, =NOH, =NOCONH$_2$, CO$_2$H or =O;

$C_{3-10}$ cycloalkyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;

$C_{3-10}$ cycloalkenyl which is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;

$C_{3-12}$ cycloalkyl($C_{1-10}$)alkyl wherein the cycloalkyl portion is optionally substituted with 1–3 members of the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H or =O;

aryl which is optionally substituted with 1–3 members of the group consistng of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl amido, $C_{1-10}$ alkylamido, $C_{1-10}$ acylamino, $C_{1-10}$ alkylsulfonylamino, C=NOH, C=NOCONH$_2$, phenyl or benzyl;

ar($C_{1-4}$)alkyl wherein the aryl moiety is optionally substituted with 1–3 members of the group consisting of carboxy, $C_{1-10}$ alkylcarboxy, halogen, hydroxy, hydroxy($C_{1-10}$)alkoxy, nitro, trihalocarbon, benzyloxy, heterocyclyl, $C_{1-10}$ cycloalkyl($C_{3-12}$) alkyloxy, ar($C_{1-10}$)alkyloxy, aryloxy, amino($C_{1-10}$) alkoxy, $C_{1-10}$ alkylamino($C_{1-10}$)alkoxy, heteroaryloxy, heteroar($C_{1-10}$)aryloxy, heterocyclyloxy, $C_{1-10}$ alkyl, $C_{3-12}$ cycloalkyl, $C_{1-10}$ alkoxy or $C_{3-12}$ cycloalkoxy said alkoxy and cycloalkoxy optionally substituted in one position at the alkyl moiety with hydroxy and said heterocyclyl is optionally substituted with $C_{1-10}$ alkyl; and wherein the alkyl moiety of said ar($C_{1-4}$)alkyl is optionally substituted with OH, halogen $C_{1-10}$ alkoxy and $C_{3-12}$ cycloalkoxy said alkoxy and cycloalkoxy being optionally substituted in one position at the alkyl moiety with hydroxy;

heterocyclyl which is optionally substituted on the carbons or nitrogens of the ring with 1–3 members of the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl;

heterocyclyl($C_1$–$C_4$)alkyl wherein said heterocyclyl moiety is optionally substituted on the carbons or nitrogens of the ring with 1–3 members of the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, C=NOH, C=NOCONH$_2$, phenyl or benzyl, and wherein said alkyl moiety is optionaly substitted with OH, $C_{1-10}$ alkoxy, $C_{3-12}$ cycloalkoxy, $C_{3-12}$ cycloalkyl, halogen or halo($C_{1-10}$)alkyl;

heteroaryl, which is optionally substituted with 1–3 members of the group consisting of $C_{1-10}$ alkyl, $C_{3-12}$ cycloalkyl, halogen, nitro, CF$_3$, $C_{1-10}$ alkoxy, $C_{3-12}$ cycloalkoxy or oxo; and heteroaryl($C_{1-4}$)alkyl, wherein the heteroaryl moiety is optionally substituted with 1–3 members of the group consisting of $C_{1-10}$ alkyl, $C_{3-12}$ cycloalkyl, halogen, nitro, trihalocarbon, $C_{1-10}$ alkoxy or $C_{3-12}$ cycloalkoxy;

provided that when $R^3$ is an unsubstituted benzyl group, $R^{6a}$ is a methyl or isopropyl group and $R^{6b}$ is a hydrogen atom;

when $R^3$, $R^{6a}$ and $R^{6b}$ are methyl groups, then $R^8$ is other than a hydrogen atom;

when $R^8$ is methyl or a hydrogen atom, $R^3$ is nether methyl or hydrogen;

when $R^8$ is phenyl, $R^3$ is not methyl;

when $R^8$ is pyridyl, $R^3$ is not a hydrogen atom; and when $R^{6a}$ and $R^{6b}$ are both hydrogen, then $R^8$ is not hydrogen or alkylC(O)OH;

and pharmaceutically acceptable salts thereof.

In certain preferred embodiments, $R^3$ is an ar($C_{1-4}$)alkyl, wherein the aryl moiety is optionally substituted at 1–3 positions with halogen, nitro, alkoxy, cycloalkoxy or $CF_3$, and wherein the alkyl moiety is optionally substituted with OH, halogen, alkoxy and cycloalkoxy. The aralkyl may be a benzyl, which may be optionally substituted as described above. In other preferred embodiments, the aralkyl is a benzyl substituted with alkoxy and cycloalkoxy.

In other preferred embodiments, $R^{6a}$ is a hydrogen. In other preferred embodiments, $R^{6a}$ is hydrogen and $R^{6b}$ is selected from the group consisting of $C_{1-10}$ alkyl, preferably $C_{1-8}$ alkyl, which is unbranched or branched and is optionally substituted with OH, alkoxy, cycloalkoxy, halogen, =NOH, =NOCONH$_2$, $CO_2H$ or =O; $C_{2-10}$ alkenyl which is unbranched or branched and is optionally substituted with OH, alkoxy, cycloalkoxy, halogen, =NOH, =NOCONH$_2$, $CO_2H$ or =O; $C_{3-10}$ cycloalkyl, preferably $C_{3-8}$ cycloalkyl, which is optionally substituted with OH, alkoxy, cycloalkoxy, halogen, haloalkyl, =NOH, =NOCONH$_2$, $CO_2H$ or =O; $C_{3-10}$ cycloalkenyl which is optionally substituted with OH, alkoxy, cycloalkoxy, halogen, haloalkyl, =NOH, =NOCONH$_2$, $CO_2H$ or =O; aryl which is optionally substituted with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl; aralkyl $C_{1-4}$ wherein the aryl moiety is optionally substituted with halogen, nitro, alkoxy, cycloalkoxy or $CF_3$, and wherein the alkyl moiety is optionally substituted with OH, halogen, alkoxy and cycloalkoxy; heterocyclyl which is optionally substituted on the carbons or nitrogens of the ring with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl; and heterocyclylalkyl ($C_1$–$C_4$) wherein said heterocyclyl moiety is optionally substituted on the carbons or nitrogens of the ring with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl, and wherein said alkyl moiety is optionally substituted with OH, alkoxy, cycloalkoxy, halogen or haloalkyl; heteroaryl, which is optionally sbstituted with $C_{1-4}$ alkyl, halogen, nitro, $CF_3$, alkoxy or cycloalkoxy, and heteroaryl($C_{1-4}$)alkyl wherein the heteroaryl moiety is optionally substituted with $C_{1-4}$ alkyl, halogen, nitro, $CF_3$, alkoxy or cycloalkoxy;

In other preferred embodiments, $R^{6a}$ is hydrogen and $R^{6b}$ is selected from the group consisting of $C_{1-10}$ alkyl, preferably $C_{1-8}$ alkyl, which is unbranched or branched and is optionally substituted with OH, alkoxy, cycloalkoxy, halogen, =NOH, =NOCONH$_2$, $CO_2H$ or =O; $C_{2-10}$ alkenyl which is unbranched or branched and is optionally substituted with OH, alkoxy, cycloalkoxy, halogen, =NOH, =NOCONH$_2$, $CO_2H$ or=O; $C_{3-10}$ cycloalkyl, preferably $C_{3-8}$ cycloalkyl, which is optionally substituted with OH, alkoxy, cycloalkoxy, halogen, haloalkyl, =NOH, =NOCONH$_2$, $CO_2H$ or =O; and $C_{3-10}$ cycloalkenyl, which is optionally substituted with OH, alkoxy, cycloalkoxy, halogen, haloalkyl, =NOH, =NOCONH$_2$, $CO_2H$ or =O.

In particular, $R^{6a}$ may be a hydrogen and $R^{6b}$ may be a $C_{1-8}$ alkyl which is unbranched or branched and is optionally substituted with OH, alkoxy, cycloalkoxy, halogen, =NOH, =NOCONH$_2$, $CO_2H$ or =O.

In other preferred embodiments of the invention, $R^{6b}$, N, and $R^{6a}$ form a 3 to 8 membered ring containing at least one carbon atom, from one to three nitrogen atoms, from zero to two oxygen atoms, and from zero to two sulfur atoms, optionaly substituted with hydroxy, alkoxy, cycloalkoxy, $C_{1-4}$ alkyl, $CO_2H$, $CONH_2$, =NOH, =NOCONH$_2$, =O.

In other preferred embodiments, $R^8$ is selected from the group consisting of $C_{1-10}$ alkyl preferably $C_{1-8}$ alkyl, which is unbranched or branched and is optionally substituted with OH, alkoxy, cycloalkoxy, halogen, =NOH, =NOCONH$_2$, $CO_2H$ or =O; $C_{2-10}$ alkenyl, which is unbranched or branched and is optionally substituted with OH, alkoxy, cycloalkoxy, halogen, =NOH, =NOCONH$_2$, $CO_2H$ or =O; $C_{3-10}$ cycloalkyl, preferably $C_{3-8}$ cycloalkyl, which is optionally substituted with OH, alkoxy, cycloalkoxy, halogen, haloalkyl, =NOH, =NOCONH$_2$, $CO_2H$ or =O; $C_{3-10}$ cycloalkenyl, which is optionally substituted with OH, alkoxy, cycloalkoxy, halogen, haloalkyl, =NOH, =NOCONH$_2$, $CO_2H$ or =O; $C_{4-8}$ cycloalkylalkyl wherein the cycloalkyl portion is optioally substituted with OH, alkoxy, cycloalkoxy, halogen, haloalkyl, =NOH, =NOCONH$_2$, $CO_2H$ or =O; aryl which is optionally substituted with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl; aralkyl $C_{1-4}$ wherein the aryl moiety is optionally substituted with hydroxy, halogen, nitro, alkoxy, cycloalkoxy or $CF_3$, and wherein the alkyl moiety is optionally substituted with OH, halogen, alkoxy and cycloalkoxy; heterocyclyl which is optionally substituted on the carbons or nitrogens of the ring with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl; heterocyclylalkyl ($C_1$–$C_4$) wherein said heterocyclyl moiety is optionally substituted on the carbons or nitrogens of the ring with $C_{1-8}$ alkyl, OH, halogen, alkoxy, cycloalkoxy, $NH_2$, alkylamino, dialkylamino, carbamyl, amido, $C_{1-8}$ alkylamido, $C_{1-3}$ dialkylamido, $C_{1-8}$ acylamino, $C_{1-8}$ alkylsulfonylamino, C=NOH, C=NOCONH$_2$, phenyl or benzyl, and wherein said alkyl moiety is optionally substituted with OH, alkoxy, cycloalkoxy, halogen or haloalkyl; heteroaryl, which is optionally substituted with $C_{1-4}$ alkyl, halogen, nitro, $CF_3$, alkoxy or cycloalkoxy; and heteroaryl($C_{1-4}$)alkyl, wherein the heteroaryl moiety is optionally substituted with $C_{1-4}$ alkyl, halogen, nitro, $CF_3$, alkoxy or cycloalkoxy.

In other preferred embodiments, $R^8$ is selected from the group consisting of $C_{1-8}$ alkyl which is unbranched or branched and is optionally substituted with OH, alkoxy, cycloalkoxy, halogen, =NOH, =NOCONH$_2$, $CO_2H$ or =O; and $C_{3-8}$ cycloalkyl which is optionally substituted with OH, alkoxy, cycloalkoxy, halogen, haloalkyl, =NOH, =NOCONH$_2$, $CO_2H$ or =O.

Certain preferred adenine compounds according to the invention include: 6-ethylamino-3-hexyl-3H-purine;

3-hexyl-6-methylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-ethyl-6-methylamino-3H-purine; 3-butyl-6-ethylamino-3H-purine; 3-butyl-8-cyclopropyl-6-ethylamino-3H-purine; 6-ethylamino-3-propyl-3H-purine; 8-cyclopropyl-6-ethylamino-3-propyl-3H-purine; 8-cyclopropyl-3-cyclopropylmethyl-6-ethylamino-3H-purine; 3-benzyl-6-ethylamino-3H-purine; 8-cyclopropyl-6-cyclopropylamino-3-propyl-3H-purine; 3-(2-methylbutyl)-6-(2-(piperazine-1-yl)ethylammio)-3H-purine; 3-cyclohexylmethyl-6-ethylamino-3H-purine; 3-benzyl-6-ethylamino-8-(1-methylethyl)-3H-purine; 3-cyclohexylmethyl-8-cyclopropyl-6-ethylamino-3H-purine; 3-cyclopropylmethyl-8-isopropyl-6-ethylamino-3H-purine; 3-ethyl-8-isopropyl-6-benzylamino-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-(4-chlorobenzyl)-6-ethylamino-3H-purine; 3-(2-chlorobenzyl)-6-ethylamino-3H-purine; 3-(2-chlorobenzyl)-6-ethylamino-8-isopropyl-3H-purine; 6-benzylamino-8-cyclopropyl-3-propyl-3H-purine; 8-cyclopropyl-6-hexylamino-3-propyl-3H-purine; 8-cyclopropyl-3-propyl-6-(4-pyridylmethylamino)-3H-purine; 6cyclopentylamino-8-cylopropyl-3-propyl-3H-purine; 6-butylamino-8-cyclopropyl-3-propyl-3H-purine; 8-cyclopropyl-6-(2-hydroxyethylamino)-3-propyl-3H-purine; 6-(3-cyclopentyloxy-4-methoxybenzylamino)-8-cyclopropyl-3-propyl-3H-purine; 6-amino-8-cyclopropyl-3-propyl-3H-purine; 3-ethyl-6-cyclopentylamino-8-isopropyl-3H-purine; 6-cyclohexylamino-8-isopropyl-3-propyl-3H-purine; 6-cyclopentylamino-8-isopropyl-3-propyl-3H-purine; 3-ethyl-6-cyclopentylamino-8-cyclopropyl-3H-purine; 3-(4-chlorobenzyl)-6-cyclopentylamino-8-cyclopropyl-3H-purine; 6-cyclopentylamino-3-(3-cyclopentyloxy-4-methoxybenzyl)-8-isopropyl-3H-purine; 3-(2-chlorobenzyl)-6-cyclopentylamino-8-isopropyl-3H-purine; 8-cyclopropyl-6-diethylamino-3-propyl-3H-purine hydrochloride; 8-cyclopropyl-6-(3-pentylamino)-3-propyl-3H-purine hydrochloride; 6-ethylamino-8-isopropyl-3-(4-pyridylmethyl)-3H-purine; 3-ethyl-8-isopropyl-6-ethylamino-3H-purine; -3-ethyl-8-cyclopentyl-6-benzylamino-3H-purine; 3-ethyl-8-cyclopentyl-6-ethylamino-3H-purine; 3-cyclohexylmethyl-6-ethylamino-3H-purine; 3-cyclohexylmethyl-8-cyclopropyl-6-ethylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-cyclopropylmethyl-6-ethylamino-3H-purine; 3-hexyl-6-methylamino-3H-purine; 3-cyclopropylmethyl-8-isopropyl-6-ethylamino-3H-purine; 3-ethyl-8-isopropyl-6-benzylamino-3H-purine; 3-butyl-6-ethylamino-3H-purine; 3-butyl-8-cyclopropyl-6-ethylamino-3H-purine; 8-cyclopropyl-6-ethylamino-3-propyl-3H-purine; 8-cyclopropyl-6-cyclopropylamino-3-propyl-3H-purine; 3-(3-cyclopentyloxy-4-methoxybenzyl)-6-ethylamino-8-isopropyl-3H-purine; and 3-ethyl-6-ethylamino-8-(3-cyclopentyloxy-4-methoxy-benzyl)-3H-purine.

Other preferred adenine compounds according to the imvention include: 3,8-diethyl-6-morpholino-3H-purine; 3-ethyl-6-ethylamino-8-((3-cyclopentyloxy-4-hydroxy)benzyl)-3H-purine; 6-ethylamino-3-(3-benzyloxy-4-methoxybenzyl)-8-isopropyl-3H-purine; 3-[(3-benzyloxy-4-methoxy)benzyl-8-[(1-benzyloxy-1-methyl)-ethyl]-6-ethylamino-3H-Purine; 3-[3-(3-trimethylsilylethoxymethoxy)cyclopentyloxy-4-methoxy)benzyl)-6-ethylamino-8-isopropyl-3H-purine; 6-Ethylamino-3-[3-(furan-2-yl-methoxy)-4-methoxy-benzyl]-8-isopropyl-3H-purine; 6-Amino-3-(3-cyclopentyloxy-4-methoxy-benzyl)-8-[1-(4-methoxybenzyloxy)-1-methyl-ethyl]-3H-purine; 6-Amino-3-(3-cyclopentyloxy-4-methoxy-benzyl)-8-(1-methylethenyl)-3H-purine; 6-Amino-8-benzyloxymethyl-3-(3-cyclopentyloxy-4-methoxy-benzyl)-3H-purine; 6-Ethylamino-3-[3-(3-hydroxycyclopentyloxy)-4-methoxy-benzyl]-8-isopropyl-3H-purine; 6-Amino 3-[3-(3-hydroxycyclopentyloxy)-4-methoxy-benzyl]-8-isopropyl-3H-purine; 6-amino-8-[(1-benzyloxy-1-methyl)ethyl]-3-[(3-cyclopentyloxy-4-methoxy)benzyl]-3H-purine; 6-Amino-3-(3-cyclopentyloxy-4-methoxybenzyl)-8-[1-(4-fluorobenzyloxyl-1-methyl-ethyl]-3H-purine; [8-(1-benzyloxy-1-methyl)ethyl]3-[(3-cyclopentyloxy-4-methoxy)benzyl]-6-ethylamino-3H-purine; 6-Amino-8-benzyloxymethyl-3-(3-cyclopentyloxy-4-methoxy-benzyl)-3H-purine; 3-[(3-cyclopentyloxy-4-methoxy)benzyl]-6-ethylamino-8-[(1-hydroxy-1-methyl)ethyl]-3H-purine; 6-Ethylamino-3-(3-butoxy-4-methoxy-benzyl)-8-isopropyl-3H-purine; 6-amino-3-[(3-cyclopentyloxy-4-methoxy)benzyl]-8-[(1-hydroxy-1-methyl)ethyl]-3H-purine; 3-[(3-cyclopentyloxy-4methoxy)benzyl]-6-ethylamino-8-(1-methyl-ethenyl)-3H-purine; 6-ethylamino-2-(3,4 dimethoxybenzyl)-8-isopropyl-3H-purine; 6-Amino-3-(3-cyclopentyloxy-4-methoxybenzyl)-3H-purine; 3-(3-cyclopentyloxy-4-methoxybenzyl)-6-dimethylamino-8-isopropyl-3H-purine; 6-Ethylamino-3-[3-(3-hydroxycyclopentyloxy)-4-methoxybenzyl)]-8-(1-hydroxy-1-methylethyl)-3H-purine; 6-ethylamino-3-(3-4-methylenedioxybenzyl)-8-isopropyl-3H-purine; 6-ethylamino-9-[(3-cyclopentyloxyl-4-methoxy)benzyl]-8-isopropyl-3H-purine; 3-(3-benzyloxy-4-methoxy-benzyl)-6-ethylamino-8-isopropyl-3H-purine; 6-Amino-3-(3,4-dimethoxybenzyl)-8-[1-(4-fluorobenzyloxy)-1-methylethyl]-3H-purine; 3-(3-cyclopentyloxy-4-methoxybenzyl)-6-amino-8-isopropyl-3H-purine; 6-(amino-8-(1-benzyloxy-1-methylethyl)-3-(3,4-dimethoxybenzyl)-3H-purine; 3-(3-cyclopentyloxy-4-methoxybenzyl)-6-(3-cyclopentyloxy-4-methoxybenzylamino)-8-isopropyl-3H-purine; 6-ethylamino-8-isopropyl-3-(4-methoxybenzyl)-3H-purine; 3-(3-((3-hydroxy)cyclopentyloxy)-4-methoxybenzyl)-6-ethylamino-8-isopropyl-3H-purine; 3-(3-cyclopentyloxy-4-methoxybenzyl)-6-(N-benzoyl-N-ethylamino)-8-isopropyl-3H-purine; 3-(4-chlorobenzyl)-6-cyclopropylamino-8-isopropyl-3H-purine; 6-ethylamino-8-isopropyl-3-[(4-methoxy-3-(4-hydroxybutoxy))benzyl]-3H-purine; 6-ethylamino-3-(4-fluorobenzyl)-8-isopropyl-3H-purine; 3-(3-chlorobenzyl)-6-ethylamino-8-isopropyl-3H-purine; 3-[3-(3-Hydroxy-cyclopentyloxy)-4-methoxy-benzyl]-8-(1-hydroxy-1-methyl-ethyl)-3H-purine; 3-[3-(3-hydroxy)cyclopentyloxy)]-4-methoxy)benzyl)-6-ethylamino-8-isopropyl-3H-purine; 6-amino-3-(3,4-dimethoxybenzyl)-8-isopropyl-3H-purine; 6-Ethylamino-3-[3-cyclopentylmethoxy-4-methoxy-benzyl]-8-isopropyl-3H-purine; 6-ethylamino-3-(3-hydroxy-4-methoxybenzyl)-8-isopropyl-3H-purine; 6-Ethylamino-3-[3-(2,2-dimethylaminoethoxy-4-methoxy)]-8-isopropyl-3H-purine; 3-[(3-cyclopentyloxy-4-methoxy)benzyl]-8-[(1-methyl-1-hydroxy)ethyl]-6-ethylamino-3H-purine; 6-amino-3-[(3-benzyloxy-4-methoxy)benzyl]-8-[(1-benzyloxy-1-methyl)ethyl]-3H-purine; 3-(3-cyclopentyloxy-4-methoxybenzyl)-6-((2,2,2-trifluoromethyl)amino)-8-isopropyl-3H-purine; 6-Ethylamino-3-[3-(2,2,2)-azabicyclooctan-3-yloxy)-4-methoxy]-8-isopropyl-3H-purine; 6-Ethylamino-3-[3-(1-methylpiperidin-4-yl-methoxy)-4-methoxy-benzy]-8- isopropyl-3H-purine; 6-Amino-3-(3,4-dimethyoxybenzyl)-8-(1-methylethenyl)-3H-purine; 6-amino-8-isopropyl-3-[(4-methoxy-3-([(4-hydroxybutoxy))benzyl]-3H-purine; 3-{2-(4-chlorophenyl)-ethyl]-6-ethylamino-8-isopropyl-3H-purine; 3-(4-chlorobenzyl)-6-((1-hydroxy)cyclopentylamino)-8-isopropyl-3H-purine; 3-(4-chlorobenzyl)-6-cyclopentylamino-8-isopropyl-3H-purine; 6-amino-3(3,4-methylenedioxybenzyl)-8-isopropyl-3H-purine; 6-Ethylamino-3-[(exo-8-methyl-8-azabicyclo(3,2,1)-octan-3-yl-oxy)-4-methoxy-benzy]-8-isopropyl-3-H-purine; 6-amino-3-((3-benzyloxy-4-methoxy)-benzyl)-8-isopropyl-3H-purine; 3-(4-chlorophenyl)-6-ethylamino-8-isopropyl-3H-purine; 6-ethylamino-3-[(3-hydroxy-4-methoxy)benzyl]-8-[(1-hydroxy-1-methyl)ethyl]-3H-purine; 6-Ethylamino-3-[(3-pyridin-4-yl-methoxy)N-oxide-4-methoxy]-8-isopropyl-3H-purine; 3-[3-Cyclohexanyl-4-oxy-4-methoxy-benzyl]-6-ethylamino-8-isopropyl-3H-purine; 3-(4-chlorobenzyl)-2,6-di(ethylamino)-8-isopropyl-3H-purine; 6-amino-3-(3-hydroxy-4-methoxy)-benzyl)-8-isopropyl-3H-purine; 6-amino-3-[3-(4-hydroxybutoxy-4-methoxy)benzyl]-8-(1-hydroxy-1-methylethyl)-3H-purine; 6-amino-3-(4-chlorobenzyl)-8-isopropyl-3H-purine; 6-amino-3-cylopentylmethyl-8-isopropl-3H-purine; 8-cyclopropyl-3-ethyl-6-ethylamino-3H-purine; 6-Ethylamnino-8-isopropyl-3-[3-(pyridin-4-yl-methoxy)-4-methoxy-benzyl]-3H-purine; 6-Ethylamino-3-(1-oxopyridin-4-yl-methyl)-8-isopropyl-3H-purine; and 6-amino-3-[(3-hydroxy-4-methoxy)benzyl)]]-8-[(1-hydroxy-1-methyl)ethyl]-3H-purine, 3-(3-COOmethyl-4-methoxbenzyl)-6-ethylamino-8-isopropyl-3H-purine, 3-(3-piperadine-4-methoxbenzyl)-6-ethylamino-8-isopropyl-3H-purine, 3-(3-benzyloxy-4-nitro-benzyl)-6-ethylamino-8-isopropyl-3H-purine, 3-(3-COOH-4-methoxbenzyl)-6-ethylamino-8-isopropyl-3H-purine, 3-(3-pyrrole-benzyl)-6-ethylamino-8-isopropyl-3H-purine, 3-butyl-6-pentylamino-8-cyclopropyl-3H-purine, 3-butyl-6cyclopentylamino-8-cyclopropyl-3H-purine, 3-butyl-6-dimethylamino-8-cyclopropyl-3H-purine and their pharmaceutically acceptable salts.

In certain preferred embodiments, the adenine compound is selected from 3-(3-cyclopentyloxy-4-methoxybenzyl)-6-ethylamino-3H-purine (PDE IV $I_{50}$=2.15 $\mu$M); 3-(4-chlorobenzyl)-6-ethylamino-8-isopropyl-3H-purine (PDE IV $I_{50}$=1.13 $\mu$M); 3-(3-cyclopentyloxy-4-methoxybenzyl)-6-ethylamino-8-isopropyl-3H-purine (PDE IV $I_{50}$=0.32 $\mu$M); and (particularly preferred) 6-cyclopentyl-8-cyclopropyl-3-propyl-3H-purine (PDE IV $I_{50}$=0.03 $\mu$M); and their pharmaceutically acceptable salts.

The present invention is also related to isoguanine compounds which are precursors of the adenine compounds described above. In addition to their role as precursor compounds, it has been surprisingly discovered that these compounds also have significant PDE IV inhibitory activity.

The present invention therefore is directed in part to a compound of the formula (II)

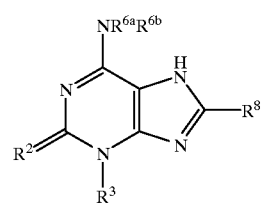

(II)

wherein $R_2$ is O or S; and $R_3$, $R_{6a}$, $R_{6b}$ and $R_8$ are the same or different and are present the same groups as those set forth with respect to compound (I) above.

Preferred isoguanine compounds according to the present invention include 6-cyclopentyamino-8-cyclopropyl-3,7-dihydro-3-propyl-2-thio-2H-purine-2-one (PDE IV $I_{50}$=7.41 $\mu$M); 8-cyclopropyl-3,7-dihydro-6-(2-hydroxythylamino)-2-thio-2H-purine-2-one (PDE IV $I_{50}$=4.48 $\mu$M); (particularly preferred) 8-cyclopropyl-3,7-dihydro-6-(4-pyridylmethylamino)-2-thio-2H-purin-2-one (PDE IV $I_{50}$= 0.41 $\mu$M); and their pharmaceutically acceptable salts.

The present invention is also related to 2,6-dithioxanthine compounds which are precursors of the adenine compounds described above. In addition to their role as precursor compounds, it has been surprisingly discovered that these compounds also have significant PDE IV inhibitory activity.

The present invention therefore is directed in part to a compound of the formula (III)

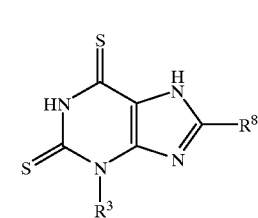

(III)

wherein $R_3$ and $R_8$ are the same or different and are represent the same groups as those set forth with respect to compound (I) above.

Preferred dithioxanthine compounds according to the present invention include 3-benzyl-3,7-dihydro-8-(1-methylethyl)-2,6-dithio-1H-purin-2,6-dione (PDE IV $I_{50}$= 3.40 $\mu$M); 3-cyclohexylmethyl-8-cyclopropyl-3,7-dihydro-2,6-dithio-1H-purin-2,6-dione (PDE IV $I_{50}$=3.03 $\mu$M); 3-(4-chlorobenzyl)-8-isopropyl-3,7-dihydro-2,6dithio-3,7-purin-2,6dione (PDE IV $I_{50}$=2.40 $\mu$M); 8-cyclopropyl-3-cyclopropylmethyl-3,7-dihydro-2,6-dithio-1H-purin-2,6-dione (PDE IV $I_{50}$=2.27 $\mu$M); 3-(3-cyclopentyloxy-4-methoxybenzyl)-3,7-dihydro-8-isopropyl-2,6-dithio-1H-purin-2,6-dione (PDE IV $I_{50}$=0.80 $\mu$M); (particularly preferred) 8-cyclopropyl-3,7-dihydro-1,3-diethyl-2,6-dithio-1H-purin-2,6-dione (PDE IV $I_{50}$=0.42 $\mu$M); and their pharmaceutically acceptable salts.

As used herein, the following terms are intended to have the meaning as understood by persons of ordinary skill in the art, and are specifically intended to include the meanings set forth below:

As used herein, the term "alkyl" means a linear or branched saturated aliphatic hydrocarbon group having a single radical and 1–10 carbon atoms. Examples of alkyl groups include methyl propyl, isopropyl, butyl, n-butyl-isobutyl, sec-butyl, tert-butyl, and pentyl. A branched alkyl means that one or more alkyl groups such as methyl, ethyl or propyl, replace one or both hydrogens in a —CH$_2$— group of a linear alkyl chain.

The term "cycloalkyl" means a non-aromatic mono- or multicyclic hydrocarbon ring system having a single radical and 3–12 carbon atoms. Exemplary monocyclic cycloalkyl rings include cyclopropyl, cyclopentyl, and cyclohexyl. Exemplary multicyclic cycloalkyl rings include adamantyl and norbornyl.

The term "alkenyl" means a linear or branched aliphatic hydrocarbon group containing a carbon-carbon double bond having a single radical and 2–10 carbon atoms. A "branched" alkenyl means that one or more alkyl groups such as methyl, ethyl or propyl replace one or both hydrogens in a —CH$_2$— or —CH═ linear alkenyl chain. Exemplary alkenyl groups include ethenyl, 1- and 2-propenyl 1-, 2- and 3-butenyl, 3-methylbut-2-enyl, 2-propenyl, heptenyl, octenyl and decenyl.

The term "cycloalkenyl" means a non-aromatic monocyclic or multicyclic hydrocarbon ring system containing a carbon-carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "cycloaklylalky" or "cycloalkyl-alkyl" means a non-aromatic mono- or multicyclic ring system, wherein the ring is substituted with an alkyl group, as defined above to include a linear or branched aliphatic hydrocarbon group having a single radical.

The term "aryl" means a carbocyclic aromatic ring system containing one, two or three rings which may be attached together in a pendent manner or fused, and containing a single radical. Exemplary aryl groups include phenyl and naphthyl.

The term "aralkyl" or "aryl-alkyl" or "aryl-alkyl" means an alkyl group as defined above to include a linear or branched saturated aliphatic hydrocarbon group having a single radical, wherein the alkyl is substituted with an aryl group, as defined above to include a carbocyclic aromatic ring system containing one, two or three rings which may be attached together in a pendent manner or fused, and containing a single radical.

The term "heterocyclic" or "heterocyclyl" means cyclic compounds having one or more heteroatoms (atoms other than carbon) in the ring, and having a single radical. The ring may be saturated, partially saturated and unsaturated, and the heteroatoms may be selected from the group consisting of nitrogen, sulfur and oxygen. Examples of saturated heterocyclic radicals include saturated 3- to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms and 1 to 3 nitrogen atoms, such as morpholinyl; saturated 3- to 6-membered heteromonocyclic groups containing 1 to 2 sulfur atoms and 1 to 3 nitrogen atoms, such as thiazolidinyl. Examples of partially saturated heterocyclic radicals include dihydrothiophene, dihydropyran, and dihydrofuran.

The term "heteroaryl" means unsaturated heterocyclic radicals, wherein heterocyclic is as previously described. Exemplary heteroaryl groups include unsaturated 3 to 6 membered heteromonocyclic groups containing 1 to 4 nitrogen atoms, such as pyrrolyl, pyridyl, pyrimidyl, and pyrazinyl; unsaturated condensed heterocyclic groups containing 1 to 5 nitrogen atoms, such as indolyl, quinolyl, isoquinolyl; unsaturated 3 to 6 membered heteromonocyclic groups containing an oxygen atom, such as furyl; unsaturated 3 to 6 membered heteromonocyclic groups containing a sulfur atom, such as thienyl; unsaturated 3 to 6 membered heteromonocyclic groups containing 1 to 2 oxygen atoms and 1 to 3 nitrogen atoms, such as oxazolyl; unsaturated condensed heterocyclic groups containing 1 to 2 oxygen atoms and 1 to 3 nitrogen atoms, such as benzoxazolyl; unsaturated 3 to 6 membered heteromonocyclic groups containing 1 to 2 sulfur atoms and 1 to 3 nitrogen atoms, such as thiazolyl; unsaturated condensed heterocyclic group containing 1 to 2 sulfur atoms and 1 to 3 nitrogen atoms, such as benzothiazolyl. The term "heteroaryl" also includes unsaturated heterocyclic radicals, wherein heterocyclic is as previously described, in which the heterocyclic group is fired with an aryl group, in which aryl is as previously described. Exemplary fused radicals include benzofuran, benzdioxole and benzotbiophene.

The term "heterocyclylalkyl" means heterocyclic groups, as defined above to include compounds having one or more heteroatoms (atoms other carbon) in the ring, and having a single radical, wherein the ring may be saturated, partially saturated and unsaturated, and the heteroatoms may be selected from the group consisting of nitrogen, sulfur and oxygen, in which the heterocyclic group is substituted with an alkyl group, as defined above to include linear or branched saturated aliphatic hydrocarbon group having a single radical. Exemplary heterocyclylalkyl groups include pyrrolidinyl-methyl, imidazolidinyl-methyl, piperidino-methyl, piperazinyl-methyl, morpholinyl-methyl, and thiazolidinyl-methyl.

The term "heteroaralkyl" or "heteroarylalkyl" means heteroaryl radicals, wherein heteroaryl is as previously described, wherein the heteroaryl group is substituted with an alkyl group as defined above to include linear or branched saturated aliphatic hydrocarbon groups having a single radical. Exemplary heteroaralkyl groups include pyrrolyl-methyl, pyridyl-methyl, pyrimidyl-methyl, pyrazinyl-methyl, indolyl-methyl, quinolyl-methyl, isoquinolyl-methyl, furyl-methyl, thienyl-methyl, oxazolyl-methyl, benzoxazolyl-methyl, thiazolyl-methyl, benzothiazolyl-methyl, benzofuran-methyl and benzothiophene-methyl.

The term "acyl" means an H—C(O)— or alkyl-C(O)-group in which the alkyl group is as previously described. Exemplary acyl groups include formyl, acetyl, propanoyl, and 2-methylpropanoyl.

The term "alkoxy" means an alkyl-O-group in which the alkyl group is as previously defined, to include a linear or branched saturated aliphatic hydrocarbon group having a single radical. Exemplary alkoxy groups include methoxy, ethoxy, n-propoxy, i-propoxy, and n-butoxy.

The term "cycloalkoxy" means a cycloalkyl-O-group in which the cycloalkyl group is as previously defined, to include non-aromatic mono- or multicyclic hydrocarbon ring systems having a single radical. Exemplary cycloalkoxy groups include cyclopentyloxy.

The term "amido" or "aminocarbonyl" means —C(O) NH$_2$.

The term "amino" means the group —NH$_2$—. The term "alkylamino" means an amino group which has been substituted with an alkyl group as defined above, and the term dialkylamino means an amino group which has been substituted with two alkyl groups, as defined above. The term "acylamino" means an amino group which has been substituted with an acyl group as defined above.

The term "carbamyl" is the group CH$_2$NO.

The term "sulfonyl" means the divalent radical SO$_2$. The term "alkylsulfonylamino" means a sulfonyl group which is substituted with an amino group as defined above, and an alkyl group as defined above.

As used herein, the term "patient" includes both human and other mammals.

The present invention also includes organic and inorganic salts, hydrates, esters, prodrugs and metabolites of the compounds of formula I.

DETAILED DESCRIPTION OF THE INVENTION

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide vanity of controlled and/or sustained release formulations are well known to those skilled in the art and are contemplated for use in connection with the formulations of the present invention The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The following examples illustrate various aspects of the present invention, and are not to be construed to limit the claims in any manner whatsoever.

EXAMPLE 1

3,8-Diethyl-6-morpholino-3H-purine (i) 3,8-Diethyl-hypoxanthine 3,8diethyl-2-thioxanthine (18.9 g) was dissolved in 370 ml of 2 NNaOH Nickel aluminum alloy (75.6 g) (1.4M of Al and 0.6M of Ni) was added in portions over 1.5 hrs at 65° C. After a further 0.5 hr at 65–70° C. the reaction product was filtered, washed with 200 ml of 1N NaOH and the filtrate neutralized with 183 ml of 5N HCl to pH 7. The formed aluminum hydroxide was filtered off, the filtrate concentrated to dryness, the residue suspended in 500 ml of absolute ethanol at 90° C., and the insoluble NaCl filtered off and washed. The filtrate was concentrated to dryness, dissolved in 200 ml of chloroform, filtered and concentrated to dryness again. The residue was crystallized from 150 ml of ethanol to give 3,8-di-ethyl-hypoxanthine (12.68 g) with mp (sublimation at 220° C.) 305–307° C. under decomposition.

(ii) 3,8-Diethyl-6-thiohypoxanthine

The product of stage (i) (8.65 g) and phosphorus pentasulfide (12.0 g) was refluxed in 150 ml of pyridine for 1 hr. Under cooling 59.4 ml of 2N NaOH was added dropwise, the solid filtered off and washed with water. The filtrate was concentrated in vacuo to dryness and the residue suspended in 200 ml of water and collected. The filtrate was extracted three times with 600 ml of chloroform. The residue of the organic phase was combined with the solid collected (total 6.08 g), dissolved in 500 ml of chloroform and filtered through 24 g of silicagel. Fractions 2 and 3 eluted 4.63 g of crude product which was crystallized from 120 ml of methanol to give 3,8-diethyl-6-thiohypoxanthine (3.58 g) with mp (sublimation at 210° C.) 250–270° C. under decomposition A second crop gave 0.58 g.

Elemental Analysis

| % calc | C 51.90 | H 5.81 | N 26.90 | S 15.40 |
|---|---|---|---|---|
| % found | C 51.76 | H 6.01 | N 26.82 | S 15.64 |

(iii) 3,8-Diethyl-6morpholino-3H-purine

The product of stage (ii) (52 mg) in 5 ml of morpholino was refluxed for 21 hrs. Evaporation in vacuo gave 65 mg of crude 3,8-diethyl-6-morpholino-3H-purine.

EXAMPLE 2

3,8-Diethyl-6-morpholino-3H-purine

(i) 3,8-Diethyl-2,6-dithioxanthine 19.14 g of 3,8-diethyl-2-thioxanthine and 22.75 g of phosphorus pentasulfide were refluxed in 280 ml of pyridine for 4.5 hrs. After cooling to room temperature 113 ml of 2N NaOH were added during 15 minutes under vigorous stirring and cooling. The suspension was filtered, washed with pyridine and concentrated in vacuo. The residue was suspended in 150 ml of water and concentrated to remove the pyridine. Suspension in water and collection of the solid gave the crude product, which is dissolved in 150 ml of 1N NaOH, treated with two portions of 0.5 g of charcoal, and filtered. The filtrate was slowly acidified with 38 ml of 5N HCl to pH 3 and a solid collected. The dried crude product (19.85 g) was suspended in 400 ml of 2-propanol at 95° C. After cooling to room temperature the solid (17.62 g) is collected and washed.

(ii) 3,8-Diethyl-3,7-dihydro-6-morpholino-2H-purine-2-thione

The product of stage (i) (14.42 g) was refluxed in 78.4 ml (900 mmoles) of morpholine for 30 hours. After cooling to room temperature the region product was suspended in 100 ml of acetone and the title product (16.49 g) collected and washed.

3,8-diethyl-3,7-dihydro-6-morpholino-2H-purine-2-thine melting point: 295–298° C. (with decomposition).

| Calc. | C 53.22 | H 6.53 | N 23.87 | S 10.93 |
| Found | C 53.01 | H 6.77 | N 23.82 | S 10.97 |

(iii) 3.8-Diethyl-6-morpholino-3H-purine

The product of stage (ii) (7.34 g) was dissolved in 150 ml of 2N NaOH Ni—Al alloy 50% (22.95 g)(425 mmoles of Al and 196 mmoles of Ni) was added over 1.25 hours at 65° C. After another 1.5 hours at 65–70° C. additional 15 ml of 10N NaOH and in portions 11.48 of Ni—Al alloy 50% was added. After another 0.5 hour at 65–70° C. the reaction product was left over night Dichloromethane (100 ml) was added, the suspension was filtered and the nickel washed with dichloromethane (200 ml) and water (100 ml). The organic phase was separated, washed twice with water and concentrated. The residue was triturated in 50 ml of petroleum-ether to give the title product as a solid (5.40 g) mp 103–107° C.

Elemental Analysis

| % calc  | C 59.75 | H 7.33 | N 26.80 |
| % found | C 59.64 | H 7.55 | N 26.35 |

HCl salt crystallized from acetone has mp (sublimation 145° C.) 220–222°C.

EXAMPLE 3

8-Cyclopropyl-3-ethyl-6-ethylamino-3H-purine

(i) 8-Cyclopropyl-3-ethyl-6-ethylamino-3,7-dihydro-2H-purine-2-thione 8-cyclopropyl-3-ethyl-2,6-dithioxanthine (20.19 g) prepared according to the method of example 2(i), and 70% ethylamine in water (320 ml 4.0M) were placed in a 450 ml pressure reactor and heated to 150° C. for 6 hours. The reaction solution was cooled to room temperature, treated with 2 portions of charcoal (0.2 g) filtered, and evaporated to dryness. The residue was triturated in menthol (300 ml), concentrated to about 200 ml, and the solid collected (16.48 g), mp 265° with decomposition.

(ii) 8-Cyclopropyl-3-ethyl-6-ethylamino-3H-purine

The product of step (i) (11.85 g) was dissolved in 2N NaOH (270 ml) and 10N NaOH (27 ml) and heated to 65° C. Within 1.25 hours 50% Ni—Al alloy (518 mmoles of Ni and 1125 mmoles of Al) (60.8 g) was added under vigorous string at 65–70° C. After a further 0.75 hr at the same temperature the reaction mixture was cooled to room temperature and treated with chloroform (400 ml). The nickel was filtered off and washed with 350 ml of chloroform and 150 ml of water. The filtrate was separated and the chloroform layer evaporated to dryness. The residue (19.64 g) was dissolved in acetone (100 ml), treated with 2 portions of charcoal (0.15 g) filtered, and evaporated. The residue was treated with diethylether (100 ml) and crystals collected (6.10 g), mp 80–96° C. A second crop gave 1.25 g. A recrystallized sample from diisopropylether had mp 103–105° C.

| % calc  | C 60.25 | H 7.54 | N 29.28 | O 2.93 |
| % found | C 60.52 | H 7.46 | N 29.10 | O 2.92* |

HCl salt crystallized from methanol-acetone with mp 183–191 ° C.

EXAMPLE 4

A. 8-(3-cyclopentyloxy-4-methoxybenzyl)-3-ethyl-6-ethylamino-3H-purine hydrochloride B. 8-(3-cyclopentyloxy-4-hydroxybenzyl)-3-ethyl-6-ethylamino-3H-purine

(i) 3-Cyclopentyloxy-4-methoxy-benzyl alcohol

To a solution of 48.70 g (220 mmoles) of 3-cyclopentyloxy-4-methoxybenzaldehyde in 250 ml of methanol was added portionwise 8.57 g (220 mmoles) of 97% sodium borohydride within 10 min at 15–22° C. under cooling. After a further 20 min the methanol was removed in vacuo and the residue taken up in 10 ml of water and 300 ml of ether. The ether phase was evaporated to dryness: 48.5 g (99.2%) of liquid benzyl alcohol.

(ii) 3-Cyclopentyloxy-4-methoxy-benzyl cyanide

To a solution of 40.00 g(180 mmoles) of benzyl alcohol in 530 ml of dichloromethane was added within 5 min 32.7 ml (450 mmoles) of thionyl chloride. The solution was evaporated in vacuo to dryness, which was repeated after toluene addition: 46.30 g (106.9%) of crude benzyl chloride, which was dissolved in 230 ml of dimethylformamide and treated with 23.50 g (360 mmoles) of potassium cyanide. The mixture was heated for 4 hours to 50–55° C. The salt was filtered off and the filtrate evaporated in vacuo to dryness, which was repeated after the addition of water, the residue was taken up in ether and extracted with 1N NaOH. The ether phase is evaporated to dryness to yield 41.20 g (99.0%) of crude benzyl cyanide.

(iii) (3-Cyclopentyloxy-4-methoxy-phenyl)acetyl chloride 42.02 g (180 mmoles) of benzyl cyanide were reflexed in 410 ml of 94% ethanol, 106 ml of water, and 180 ml of 10N NaOH for 20 hours. The ethanol was removed in vacuo, the solution diluted to 800 ml with water, treated twice with 2 g of charcoal, filtered, and acidified with 185 ml of 10N HCl. The acid crystallized slowly, was collected and dried at 30° C.: 42.2 g (92.9%) of acid. 1.51 g (2.3%) could be extracted by ether from the filtrate. Both parts (173 mmoles) are combined and refluxed in 500 ml of dichloromethane and 31.4 ml (433 mmoles) of thionyl chloride for 1.5 hours. The solution was treated twice with 2 g of charcoal, filtered and evaporated to dryness. This was repeated twice with little toluene: 48.70 g (>100%) of crude acetyl chloride as a reddish liquid.

(iv) 8-(3-Cyclopentyloxy-4-methoxy-benzyl)-3-ethyl-2-thioxanthine 10.02 g (45 mmoles) of 5,6-diamino-1-ethyl-2-thiouracil hydrochloride was dissolved in 200 ml of pyridine, treated with 6.05 g (57 mmoles) of sodium carbonate and 15.5 g (56 mmoles) of Example 4 (iii) dissolved in 25 ml of ether added within 10 minutes at 5–10° C. After 1.5 hours at room temperature the solid was filtered off and the filtrate evaporated in vacuo to dryness. The residue was dissolved in 100 ml of 2N NaOH and 200 ml of water and brought to reflux, within 1 hour 70 ml are distilled off. The solution was filtered and neutralized to pH 7.5 with 52 ml of 5N HCl. The solid was collected and dried: 14.37 g (79.7%) of crude 2-thioxanthine (from the water 4.2 g of the phenyl acetic acid was recovered), which was suspended in 250 ml of hot methanol and collected again: 10.68 g (59.3%) of purified 2-thioxanthine, which was dissolved is 100 ml of 1N NaOH and filtered. The filtrate was acidified to pH 6 and the solid collected: 8.82 g (48.9%) of 2-thioxanthine with mp (260° C.) 280–310° C. under decomposition.

(v) 8-(3-Cyclopentyloxy-4-methoxy-benzyl)-3-ethyl-2,6-dithioxanthine 8.41 g (21 mmoles) of 2-thioxanthine are refluxed with 5.60 (25.2 mmoles) of phosphorus pentasulfide in 80 ml of pyridine. After 5.5 hours 27.7 ml (55.4 mmoles) of 2N NaOH were added at 5–10° C. The solid was filtered off and washed with pyridine. The filtrate was evaporated in vacuo to dryness, the residue is suspended in 200 ml of water with little tetrahydrofuran (THF) for crystllization, the suspension is concentrated and the solid at pH 8 collected and washed. Redissolution in 100 ml of 0.5 N NaOH, treatment with charcoal (20%), filtration and acidification to pH 6 yielded the solid crude dithioxanthine 7.84 g (89.6%). Crystallization from chloroform and suspension in hot methanol gave 5.31 g (60.7%) of dithioxanthine with mp 241–3° C. The mother liquors were combined (2.36 g) and filtered with chloroform through 60 g of silicagel in a column: 1.73 g (19.8%) were isolated as a second crop.

(vi) 8-(3-Cyclopentyloxy-4-methoxy-benzyl)-3ethyl - 6-ethylamino-3,7-dihydro-2H-purine-2-thione 6.67 g (16 mmoles) of dithioxanthine and 52 ml of 70% ethylamine in water were heated to 150° C. in a pressure reactor (250 psi) for 12 hours under nitrogen. The solution was treated with charcoal (5%), filtered, and evaporated in vacuo to dryness. The residue was suspended in water, acidified with 1N HCl to pH 4 and neutralized to pH 8 with sodium bicarbonate. The solid was collected, washed and dried to give 6.66 g (97.4%) of crude thioisoguanine.

(vii) A. 8-(3-Cyclopentyloxy-4-methoxy-benzyl)-3-ethyl-6-ethylamino-3H-purine hydrochloride and B. 8-(3-cyclopentyloxy-4-hydroxy-benzyl)-3-ethyl-6-ethylamino-3H-purine hydrochloride 6.41 g (15 mmoles) of crude thioisoguanine and 9.70 g (165 mmoles) of neutral Raney-nickel were refluxed in 70 ml of 1-propanol for 3 hours. The nickel was filtered off and the filtrate evaporated in vacuo to dryness. The residue (5.86 g/98.8%) was dissolved in chloroform and extracted extensively with 1N NaOH. The NaOH solution was acidified with 5N HCl to pH 4 and neutralized with sodium bicarbonate to pH 7.5. An oil precipitated, which crystallized slowly and the solid collected 0.49 g of 8-(3-cyclopentyloxy-4-hydroxy-benzyl)-3-ethyl-6-ethyl-amino-3H-purine with mp 172–4° C. The chloroform solution was evaporated to dryness: 3.76 g (63.4%) of crude 3H-purine, which was dissolved in 30 ml of methanol and treated with 10 ml of 1N methanolic HCl. The solution was evaporated in vacuo to dryness and the residue crystallized from acetone acetate: 3.66 g (56.5%) of 8-(cyclopentyloxy-4-methoxybenzyl)-3-ethyl-6-ethylamino-3H-purine hydrochloride with mp 169–71° C.

Elemental Analysis for $C_{22}H_{30}ClN_5O_2$

| | | | |
|---|---|---|---|
| Calc. | C 61.17 | H 7.00 | N 16.21 |
| Found | C 61.09 | H 6.77 | N 16.18 |

EXAMPLE 5

3-(3-cyclopentyloxy-4-methoxybenzyl)-6-ethylamino-8-isopropyl-3H-purine hydrochloride (i) 3Cyclopentyloxy-4-methoxy-benzaldehyde 77.70 g (500 mmoles) of isovanilin and 69.40 g (600 mmoles) of 97% potassium t-butoxide (t-BuOK) dissolved in 800 ml of 1-propanol, 69.0 ml 630 mmoles), and the solution refluxed. After 3 hours another 9.25 g (80 mmoles) of t-BuOK were added at 80° C. and the suspension refluxed for another 3 hours. The solid was filtered off and the filtrate evaporated in vacuo to dryness. The residue was dissolved in ether and extracted with 1N NaOH. The ether phase was evaporated to dryness: 85.40 g (77.5%) of cyclopentyloxy-benzaldehyde was isolated.

(ii) 3-Cyclopentyloxy-4-methoxy-benzaldehyde-oxime 85.4 g (388 mmoles) of 3-cyclopentyloxy-4-methoxy-benzaldehyde were dissolved in 350 ml of 94% ethanol and added within 10 minutes at 15–20° C. to a solution of 29.78 g (427 mmoles) of hydroxylammonium chloride and 52.8 g (388 mmoles) of sodium acetate trihydrate (3 $H_2O$) in 230 ml of water. After 2 hours the ethanol was removed in vacuo, the residue treated with 16.3 g (194 mmoles) of sodium bicarbonate until $CO_2$ formation ceased and extracted with ether. Evaporation of the ether phase gave 91.0 g (99.7%) of oxime as a mixture of the 2 isomers.

(iii) 3-Cyclopentyloxy-4-methoxy-benzylamine 73.5 g (320 mmoles) of oxime, 80 ml of methanol, 55 g of liquid ammonia, and 18.5 g of neutral Raney-nickel are placed into a 450 ml pressure reactor. Hydrogen gas was added up to a pressure of 1,200 psi and the whole heated to 75–80° C., when the pressure dropped to 600 psi hydrogen gas was added again to 1,200 psi. After 4 hours the pressure reached 1080 psi and remained constant. The nickel was filtered off and washed with methanol. The filtrate is evaporated to dryness, dissolved in ether and extracted with 1N NaOH. The ether phase was evaporated to dryness: 68.9 g (97.3%) of benzylamine.

(iv) 3-Cyclopentyloxy-4-methoxy-benzyl-isothiocyanate 82.3 g (372 mmoles) of benzylamine were dissolved in 10 ml of toluene and added at 15–20° C. (with cooling) within 20 minutes to an emulsion of 22.5 ml (372 mmoles) of carbon disulfide and 14.88 g (372) mmoles) of NaOH in 52 ml of water. The reaction mixture was heated to 75–80° C. for 1 hour and cooled to 40° C. Within 15 minutes, 35.4 ml (372 mmoles) ethyl chloroformate were added at 40–45° C. The emulsion was brought to about pH 8 with 2N NaOH and heated to 55–60° C., gas formation ceased after about 10 hours keeping the pH at 8 with 2N NaOH (total about 8 ml). The organic layer was collected and the solvent evaporated: 96.3 g (98.3%) of benzyl isothiocyanate.

(v) 1-(3-Cyclopentyloxy-4-methoxy-benzyl)-2-thiourea 96.3 g (366 mmoles) of benzylisothiocyanate were dissolved in 100 ml o THF and treated with 44.2 ml (732 mmoles) of 32% ammonia solution After 0.5 hour at 40–45° C., 300 ml of water were added and the THF removed in vacuo. The gummy suspension is treated with 200 ml of ether, the crystals collected and washed with water and ether. Suspension in 30 ml of methylenechloride and collection gave 65.77 g (64.2%) of benzyl-2-thiourea with mp 144–5° C.

(vi) 6-Amino-1-(3-cyclopentyloxy-4-methoxy-benzyl)-2-thiouracil 29.65 g (256 mmoles) of 97% t-BuOK were dissolved in 240 ml of 2-propanol. 65.33 g (233 mmoles) of 2-thiourea and 25.3 ml (238 mmoles) of ethyl cyanoacetate were added at 80° C. After 30 minutes at reflux a solution was formed and after 4.5 hours an additional 2.96 g (25.6 mmoles) of t-BuOK and 4.97 ml (46.6 mmoles) of ethyl cyanoacetate added. After 22 hours of refluxing the solid was collected, combined with the residue of the filtrate, dissolved in 1l of water and precipitated with about 50 ml of 5N HCl (pH 3–4). The solid is collected, washed, dried, recrystallized by suspension in 1l of refluxing acetone, concentrated to about 300 ml and collected at 23° C.: 80.65 g (85.7%) of uracil containing 1 equivalent of acetone, mp 225–7°C.

(vii) 6-Amino-1-(3-cyclopentyloxy-4-methoxy-benzyl)-5-nitroso-2-thiouracil 68.9 g (170 mmoles) of uracil are dissolved in 650 ml of acetic acid, for removal of acetone 100 ml are distilled off in vacuo, and at 65–70° C. 43.4 ml (174 mmoles) of 4N sodium nitrite solution were added within 10 minutes. After farther 5 minutes the suspension was cooled to 30° C. and diluted with 1.7l of water. The solid was collected, washed, and dried: 64.08 g (100%) of nitrosouracil which was dissolved in 330 ml of 1N NaOH and 300 ml of water, filtered, and acidified with 5N HCl to pH 2, to keep it in suspension 2l of water were added. The solid was collected and washed, in 60 ml of methanol and collected again: 54.2 g (84.7%) of nitrosouracil.

(viii) 1-(3-cyclopentyloxy-4-methoxy-benzyl)-5,6-diamino-2-thiouracil 15.06 g (40 mmoles) of nitrosouracil are suspended in 300 ml of THF and hydrogenated with hydrogen gas and 6 g of neutral Raney-nickel for 2.5 hours, when hydrogen uptake ceased. After 1 hour all was dissolved and thereafter a new precipitate formed, which is dissolved in a mixture of methylenechloride and methanol. The nickel was filtered off and the filtrate evaporated in vacuo to dryness: 13.96 g (96.3%) of crude diaminourail.

(ix) 6-Amino-1-(3-cyclopentyloxy-4-methoxy-benzyl)-5-isobutyrylamino-2-thiouracil A two phase solution of 15.01 g (41.4 mmoles) of diaminouracil, 180 ml of THF, 150 ml of water, 6.96 g (82.8 mmoles) of sodium bicarbonate, and 10.52 ml (62.1 mmoles) of isobutyric anhydride is heated to 55° C. under nitrogen for 1 hour. The THF was evaporated in vacuo and the residue diluted with 200 ml of water (pH 8). The solid was collected, washed, and dried: 16.25 g (90.7%) of isobutyrylaminouracil.

(x) 3-(3-Cyclopentyloxy-4-methoxy-benzyl)-8-isopropyl-2-thioxanthine 17.81 g (41.2 mmoles) of isobutyrylaminouracil were refluxed for 0.75 hour in 120 ml of 1N NaOH and 80 ml of water. The solution was treated twice with 0.5 g of charcoal, filtered, acidified with 5N HCl, and put to pH 7–8 with sodium bicarbonate solution. The solid was collected, washed, and dried: 15.31 g (89.6%) of 2-thioxanthine with mp 270–6° C. (with decomposition).

(xi) 3-(3-Cyclopentyloxy-4-methoxy-benzyl)-8-isopropyl-2.6-dithioxanthine 15.17 g (36.6 mmoles) of 2-thioxanthine and 9.76 g (43.9 mmoles) of phosphorus pentasulfide were refluxed under nitrogen in 140 ml of pyridine for 5.5 hours. At 5–10° C. 48.3 ml (96.6 mmoles) of 2N NAOH were added dropwise. The solid was filtered of and washed with pyridine. The filtrate was evaporated in vacuo to dryness and treated with 300 ml of water. The suspension was adjusted to pH 7 with sodium bicarbonate solution and the solid collected, washed, dissolved in 200 ml of 0.5N NaOH solution, treated twice with 1.6 g of charcoal; filtered, acidified with 5N HCl and neutralized with sodium bicarbonate solution to pH 7. The solid was collected, washed, and dried: 14.64 g (92.9%) of crude dithioxanthine, which was dissolved in 400 ml of methylenechloride and filtered through 60 g of silicagel in a column. The solvent was evaporated and the residue suspended in 20 ml of 100% ethanol and collected: 14.34 g (82.2%) of dithioxanthine with mp 204–6° C. (containing 1 mol EtOH).

(xii) 3-(3-Cyclopentyloxy-4-methoxy-benzyl)-3,7-dihy-dro-6-ethylamino-8-isopropyl-2H-purine-2-thione 6.20 g (13 mmoles) of dithioxanthine and 42 ml of 70% ethylamine in water were placed into a 450 ml pressure reactor and heated to 150° C. (240 psi) for 12 hours. The solution was filtered and evaporated to dryness. The residue was suspended in water, acidified with 1N HCl to pH 3, and neutralized with sodium bicarbonate solution to pH 7–8. The solid was collected, washed, and dried: 5.48 g (95.5%) of thioisoguanine with mp 72–7° C.

(xiii) 3-(3-Cyclopentyloxy-4-methoxybenzyl)-6-ethylamino-8-isopropyl-3H-purine hydrochloride 5.43 g (12.3 mmoles) of thioisoguanine and 7.9 g of neural Raney-nickel were refluxed in 60 ml of 1-propanol for 4.5 hours. The nickel was filtered off and the filtrate evaporated in vacuo to dryness: 4.90 g (97.2%) of crude purine, which was dissolved in 20 ml of chloroform, extracted with 1N NaOH and filtered through 30 g of silicagel in a column. The solvent was evaporated, the residue dissolved in 25 ml of menthol, treated with 11 ml of methanolic 1N HCl solution and evaporated to dryness. The residue was suspended in 80 ml of ethyl acetate and collected: 3.49 g (63.6%) of 3H-purine hydrochloride with mp 202–12° C.

Elemental Analysis for $C_{23}H_{32}ClN_5O_2$

|       | C     | H    | N     | O    |
|-------|-------|------|-------|------|
| Calc. | C 61.94 | H 7.23 | N 16.21 | O 7.17 |
| Found | C 62.17 | H 7.02 | N 15.66 | O 7.30 |

EXAMPLE 6

3-(3-Cyclopentyloxy-4-methoxybenzyl)-6-ethylamino-3H-purine hydrochloride (i) 3-(3-Cyclopentyloxy-4meth-oxy-benzyl)-2-thioxanthine 14.62 g (40 mmoles) of 1-(3-cyclopentyloxy-4-methoxy-benzyl)-5,6-diamino-2-thiouracil were dissolved in 200 ml of formic acid. The solution was concentrated in vacuo at room temperature to remove the water. 50 ml of formic acid were added and the procedure repeated. After a total of 1 hour the formic acid solution was concentrated to 30 ml at 25° and diluted with 300 ml of water. The crystals were collected, washed, and dried: 13.48 g (86.3%) of crude 5-formamide (mp 210–30° C.), which was refluxed in 86 ml of 1N NaOH for 15 min. The turbid solution was treated twice with 0.6 g of charcoal, filtered, acidified with 5N HCl to pH 2, and neutralized to pH 6.5. The amorphous solid was collected, washed, and dried at 60° C.: 11.93 g (80.1%) of crude 2-thioxanthine, which was dissolved in 150 ml of THF, treated with charcoal (5%), filtered, concentrated to 40 ml, and diluted with 250 ml of ethanol. After concentration to 120 ml the formed solid is collected, washed, and dried: 9.21 g (61.9%) of 2-thioxanthine with mp 254–65° C.

|       | C     | H    | N     | O    |
|-------|-------|------|-------|------|
| Calc. | C 58.05 | H 5.41 | N 15.04 | O 12.89 |
| Found | C 58.13 | H 5.41 | N 14.93 | O 13.11 |

(ii) 3-(3-Cyclopentyloxy-4-methoxy-benzyl)-2,6-dithioxanthine 8.94 g (24 mmoles) of 2-thioxanthine and 6.40 g (28.8 mmoles) of phosphorus pentasulfide were refluxed in 96 ml of pyridine under nitrogen for 1.5 hours. At 5–10° C. 31.7 ml (63.4 mmoles) of 2N NaOH were added under cooling and the mixture diluted with 30 ml of pyridine. The solid was filtered off and the filtrate evaporated in vacuo to dryness. The residue was suspended in 30 ml of water and the solid collected, dissolved in 160 ml of 0.5N NaOH, filtered, treated with charcoal (20%), filtered again, acidified with 5N HCl to pH 5, the solid collected, washed, and dried: 9.03 g (96.9%) of crude dithioxanthine. The product was dissolved in 400 ml of chloroform and filtered through 30 g of silicagel in a column. The solvent was removed in vacuo, the residue dissolved in 50 ml of THF, filtered, concentrated to 30 ml, diluted with 200 ml of ethanol, concentrated again to 150 ml and the solid collected, washed, and dried: 8.65 g (92.8%) of dithioxanthine with mp 215–8° C.

Elemental Analysis for $C_{18}H_{20}N_4O_2S_2$ with 0.25M of Ethanol and 0.5M of Water

|       | C     | H    | N     | O    |
|-------|-------|------|-------|------|
| Calc. | C 54.32 | H 5.54 | N 13.70 | O 10.76 |
| Found | C 54.67 | H 5.32 | N 13.80 | O 10.20 |

(iii) 3-(3-Cyclopentyloxy-4-methoxy-benzyl)-3,7-dihydro-6-ethylamino-2H-purine-2-thione 4.66 g (12 mmoles) of dithioxanthine and 48.3 ml (60 mmoles) of 70% ethylamine in water were heated to 150° C. in a 450 ml pressure reactor under $N_2$ for 12 hours (240 psi). The solution was treated with charcoal (5%), filtered and evaporated to dryness. The residue was taken up in 100 ml of water, acidified with 1N HCl to pH 3 and neutralized with sodium bicarbonate to pH 7, and the solid collected: 4.43 g (92.5%) of crude thioisoguanine with mp 99–103° C.

(iv) 3-(Cyclopentyloxy-4-methoxy-benzyl)-6-ethylamino-3H-purine hydrochloride 4.39 g (11 mmoles) of thioisoguanine and 7.10 g (121 mmoles) of neutral Raney-nickel are refluxed in 50 ml of 1-propanol for 4.5 hours. The nickel was filtered off and the filtrate evaporated to dryness. The residue (3.79 g/93.8%) was dissolved in 20 ml of chloroform and 0.4 ml methanol and filtered through 24 g of silicagel in a column also with 2% methanol. The combined fractions were washed with 1N NaOH and the organic phase evaporated to dryness. The residue (2.69 g/66.6%) was dissolved in 30 ml of dichloromethane and 0.6 ml methanol and again filtered through 30 g of silicagel. A total of 1.86 g (46.0%) of 3H-purine was isolated, which was dissolved in 20 ml of methanol, treated with 5.4 ml of 1N methanolic HCl, and evaporated in vacuo to dryness. Crystallization and recrystallization from dichloromethane and ethyl acetate gave 1.75 g (39.4%) of 3H-purine hydrochloride with mp 170–85° C.

Elemental Analysis for $C_{20}H_{26}C_1N_5O_2$

|       | C     | H    | N     | O    |
|-------|-------|------|-------|------|
| Calc. | C 59.47 | H 6.49 | N 17.34 | O 7.92 |
| Found | C 59.72 | H 6.44 | N 17.25 | O 8.24 |

EXAMPLE 7

8-Cyclopropyl-6-(4-pyridylmethyl-amino)-3-propyl-3H-purine dihydrochloride (i) 8-Cyclopropyl-3-propyl-2,6-dithioxanthine In a 5 L 3-necked flask fitted with a mechanical stirrer and a condenser with a drying tube were placed 2.2 L of pyridine and 8-cyclopropyl-3-propyl-2-thio-xanthine (220 g, 0.88 mol). Phosphorus pentasulfide (236 g, 1.06 mol) was added and the mixture was heated under reflux for 5 hours and stored overnight at room temperature. The reaction mixture was cooled to 5–10° and 3 N aqueous sodium hydroxide (770 ml) was added over 1.5 hours with stirring. Stirring was continued for 30 minutes after removal of the cooling bath and the precipitated product was collected by suction filtration. The filter cake was washed successively with pyridine (300 ml) and four 300 ml portions of tetrahydrofuran. The solvents are evaporated in vacuo and the solid residue was stirred with water (750 ml), filtered and washed with water. The crude product was dissolved in 1.7 L of 1 N sodium hydroxide and stirred with 15 g of Darco G-60. The charcoal was filtered and the treatment was repeated with a fresh portion of charcoal. The solution was acidified to pH 1.5 with 6 N hydrochloric acid and the pale yellow precipitate was collected. The solid was dissolved again in 1.7 L of 1N sodium hydroxide and treated successively with two portions of charcoal as above. The solution was acidified and the precipitate was collected and washed with water. After drying to constant weight at 54° C. under vacuum, there was obtained 128 g (56%) of the title compound, mp over 245° C.

(ii) 8-Cyclopropyl-3,7-dihydro-3-propyl-6-(4-pyridylmethylamino)-2H-purine-2-thione 5.33 g (20 mmoles) of 8-cyclopropyl-3-n-propyl-2,6-dithioxanthine and 21.3 ml (200 mmoles) of 95% 4-picolylamine were heated under argon to 150–5° C. After 14 hours the cooled solution was poured into 100 ml of water, acidified with 19 ml of 10N HCl and 1N HCl to pH 6, where an orange colored gum was formed. With sodium bicarbonate the mixture was neutralized to pH 7. With time the gum crystallized and the solid is collected and washed. The residue was suspended in acetone and the crystals collected: 3.92 (57.6%) of crude product. The filtrate was evaporated to dryness, dissolved in 40 ml of 0.5N NaOH, extracted 4 times with methylene-chloride, and acidified again with 5N HCl to pH 6. Again the gum crystallized over 48 hours and the mixture was neutralized to pH 7 with bicarbonate and the solid collected: 1.75 g (25.7%) of crude product. Both parts were dissolved in 30 ml of methylenechloride and filtered through 30 g of silicagel in a column. 150 mg (2.8%) of starting material was recovered first, then 5.04 g (74.0%) of product was recovered with 5% of methanol, which was dissolved in 32 ml of 1N HCl, treated with 250 mg of charcoal, filtered, and neutralized with 7.5 ml of 2N NaOH and sodium bicarbonate solution to pH 7–8. The water phase was decanted from the gum and the latter washed with water and crystallized from acetone: 4.08 g (59.9%) of thioisoguanine with mp 204–210° C. with decomposition.

(iii) 8-Cyclopropyl-6-(4-pyridylmethylamino)-3-propyl-3H-purine dihydrochloride 3.06 g (9 mmoles) of thioisoguanine and 5.8 g of neutral Raney-nickel were refluxed under argon in 1-propanol for 4 hours. The nickel was filtered off and washed with methanol. The filtrate as evaporated to dryness, the residue dissolved in 20 ml of methylenechloride, the solution extracted with 1N NaOH, and evaporated to dryness: 2.43 g (87.4%) of crude purine, which was dissolved in 20 ml of methanol, treated with 17 ml of 1N methanolic HCl and evaporated again to dryness. Crystallization from isopropanol gives 1.09 g (36.3%) of purine dihydrochloride with mp 157–65° C.

EXAMPLE 8

6-Cyclopentylamino-8-cyclopropyl-3-propyl-3H-purine hydrochloride (i) 6-Cyclopentylamino-8-cyclopropyl-3,7-dihydro-3-propyl-2H-purine-2-thione 5.33 g (20 mmoles) of 8-cyclopropyl-3-n-propyl-2,6-dithioxantine and 42 ml of cyclopentylamine were heated in a 450 ml pressure reactor to 150° C. (50 psi) with the exclusion of air. After 20 hours the solution was transferred with menthol to a round bottom flask and evaporated in vacuo to dryness. The residue is treated with 60 ml of water and 5N HCl to obtain a pH of 2. The suspension is neutralized with bicarbonate to pH 7, the solid collected, washed, dried, suspended in refluxing acetone and collected again: 5.98 g of thioisoguanine with mp 274–6° C. (decomp).

(ii) 6-Cyclopentylamino-8-cyclopropyl-3-n-propyl-3H-purine hydrochloride 4.49 g (14.1 mmoles) of thioisoguanine and 9.2 g of neutral Raney-nickel were refluxed in 45 ml of 1-propanol for 5 hours. The nickel was filtered off and the filtrate evaporated to dryness. The residue (>100%) was dissolved in 30 ml of methanol, treated with 16.9 ml of 1N methanolic HCl solution, and evaporated to dryness. The residue was dissolved in methylene-chloride, treated with 0.12 g of charcoal filtered, concentrated, diluted with acetone and the remaining methylene chloride removed by distillation. The crystals were collected: 4.18 g (92.3%) of purine hydrochloride with mp 218–221° C.

Elemental Analysis for $C_{16}H_{24}ClN_5$

M.W. 321.86

| | | | | |
|---|---|---|---|---|
| Calc. | C 59.71 | H 7.52 | N 21.76 | Cl 11.01 |
| Found | C 59.82 | H 7.40 | N 21.76 | Cl 11.02 (diff) |

EXAMPLE 9

Thioisoguanine Derivatives

Following the previously set forth methods, the following thioisoguanine derivatives of the present invention were synthesized. The chemical name and melting point are provided in Table 1 below.

TABLE 1

THIOISOGUANINES

| Compound | m.p. (° C.) |
|---|---|
| 3,8-diethyl-3,7-dihydro-6-morpholino-2H-2-thio-purin-2-one | 295–298 (dec) |
| 3-(cyclopropylmethyl)-3,7-dihydro-8-isopropyl-6-propylamino-2-thio-2H-purin-2-one | 208–210 |
| 3,7-dihydro-6-ethylamino-3-hexyl-2-thio-2H-purin-2-one | 235–237 |
| 3,7-Dihydro-3-hexyl-6-methylamino-2-thio-2H-purin-2-one | 217–219 |
| 3-benzyl-3,7-dihydro-6-methylamino-2-thio-2H-purin-2-one | 253–255 |
| 8-cyclopropyl-3,7-dihydro-6-ethylamino-3-(3-methylbutyl)-2-thio-2H-purin-2-one | 250–254 |
| 8-cyclopropyl-3,7-dihydro-3-ethyl-6-propylamino-2-thio-2H-purin-2-one | 270–272 |
| 3-butyl-3,7-dihydro-6-ethylamino-2-thio-2H-purin-2-one | (220) 246–248 |
| 3-butyl-8-cyclopropyl-3,7-dihydro-6-ethylamino-2-thio-2H-purin-2one | 226–228 |
| 6-ethylamino-3,7-dihydro-3-propyl-2-thio-2H-purin-2-one | 247–251 |
| 8-cyclopropyl-6-ethylamino-3,7-dihydro-3-propyl-2-thio-2H-purin-2-one | 238–239 |

TABLE 1-continued

THIOISOGUANINES

| Compound | m.p. (° C.) |
|---|---|
| 8-cyclopropyl-3-cyclopropylmethyl-6-ethylamino-3,7-dihydro-2-thio-2H-purin-2-one | 247–249 |
| 3-benzyl-6-ethylamino-3,7-dihydro-2-thio-2H-purin-2-one | 254–257 |
| 8-cyclopropyl-6-cyclopropylamino-3-propyl-3,7-dihydro-2-thio-2H-purin-2-one hydrochloride | 208–226 dec |
| 3-((2-methyl)butyl))-6-(2-(piperazine-1-yl)ethylamino)-3,7-dihydro-2-thio-2H-purin-2-one | |
| 3-cyclohexylmethyl-3,7-dihydro-6-ethylamino-2-thio 2H-purin-2-one | 295–300 |
| 3-benzyl-6-ethylamino-3,7-dihydro-8-(1-methylethyl)-2-thio-2H-purin-2-one | |
| 3-cyclohexylmethyl-8-cyclopropyl-3,7-dihydro-6-ethyl-amino-2-thio-2H-purin-2-one | 278–282 |
| 6-benzylamino-8-(cyclopropyl)-3,7-dihydro-3-propyl-2-thio-2H-purin-2-one hydrochloride | 180–185 |
| 8-(cyclopropyl)-3,7-dihydro-6-hexylamino-3-(propyl)-2-thio-2H-purin-2-one hydrochloride | 170–190 |
| 6-butylamino-8-cyclopropyl-3,7-dihydro-3-propyl-2-thio-2H-purin-2-one | 231–233 |
| 6-cyclopropyl-3,7-dihydro-6-(2-hydroxyethylamino)-2-thio-2H-purin-2-one | 188–192 |
| 6-amino-8-cyclopropyl-3,7-dihydro-3-propyl-2-thio-2H-purin-2-one | 220–265 |
| 6-cyclopentylamino-3-ethyl-3,7-dihydro-8-isopropyl-2-thio-2H-purin-2-one | 301–304 |
| 6-cyclohexylamino-3,7-dihydro-8-isopropyl-3-propyl-2-thio-2H-purin-2-one | 303 dec |
| 6-cyclopentylamino-3,7-dihydro-8-isopropyl-3-propyl-2-thio-2H-purin-2-one | 295 dec |
| 6-cyclopentylamino-3-theyl-8-cyclopropyl-3,7-dihydro-2-thio-2H-purin-2-one | 245 dec |
| 3-(4-chlorobenzyl)-6-cyclopentylamino-3,7-dihydro-8-isopropyl-2-thio-2H-purin-2-one | 244–248 |
| 6-cyclopenylamino-3-(3-cyclopentyl-4-methoxy-benzyl)-3,7-dihydro-8-isopropyl-2-thio-2H-purin-2-one | 230–235 |
| 3-(2-chlorobenzyl)-6-cyclopentylamino-3,7-dihydro-8-isopropyl-2-thio-purin-2-one | |
| 8-cyclopropyl-3,7-dihydro-6-(3-pentyl)-3-propyl-2-thio-2H-purin-2-one | 220 dec |
| 6-ethyl-8-isopropyl-3,7-dihydro-3-(4-pyridylmethyl)-2-thio-2H-purin-2-one | 238–40 |

EXAMPLE 10

Elemental Analysis of Thioisoguanine Derivatives

A. Elemental analysis for 6-butylamino-8-cyclopropyl-3,7-dihydro-3-propyl-2H-purine-2-thione:

| Calc. | C 58.98 | H 7.59 | N 22.93 |
|---|---|---|---|
| Found | C 58.99 | H 7.52 | N 22.92 |

B. 3-(cyclopropylmethyl)-3,7-dihydro-8-isopropyl-6-propylamino-2H-purine-2-thione Melting point: 208–210° C.

Elemental analysis:

| Calc. | C 62.26 | H 8.01 | N 24.20 |
|---|---|---|---|
| Found | C 62.34 | H 8.06 | N 23.89 |

EXAMPLE 11

PDE IV Inhibition by Thioisoguanine Compounds

The PDE IV inhibitory activity of certain of the foregoing thioisoguanine compounds was determined according to the procedures set forth below. The results are provided in Table 2.

Type IV Phosphodiesterase Enzyme Isolation Protocol

The Type IV PDE is isolated from bovine tracheal smooth muscle using a procedure similar to that previously described by Silver, P. J., Hamel, L. T., Perrone, M. H. Bentley, R. G. Bushover, C. R., Evans, D. B.: Eur. J. Pharmacol. 150:85,1988. (1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 $\mu$M, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

TABLE 2

THIOISOGUANINES - BIOLOGICAL DATA

| Name | Calc IC50 PDE IV |
|---|---|
| 3-(cyclopropylmethyl)-3,7-dihydro-8-(1-methyl-ethyl)-6-propylamino-2-thio-2H-purin-2-one hydrochloride | 23.95 |
| 8-cyclopropyl-3-ethyl-6-ethylamino-3,7-dihydro-2-thio-2H-purin-2-one | 13.65 |
| 8-cyclopropyl-3-ethyl-6-propylamino-2-thio-2H-purin-2-one | 8.48 |
| 3-butyl-8-cyclopropyl-3,7-dihydro-6-ethylamino-2-thio-2H-purin-2-one | 34.86 |
| 3-benzyl-6-ethylamino-3,7-dihydro-8-(1-methyl-ethyl)-2-thio-2H-purin-2-one | 28.37 |
| 3-cyclohexylmethyl-8-cyclopropyl-3,7-dihydro-6-ethylamino-2-thio-2H-purin-2-one | 15.20 |

TABLE 2-continued

THIOISOGUANINES - BIOLOGICAL DATA

| Name | Calc IC50 PDE IV |
|---|---|
| 6-benzylamino-8-(cyclopropyl)-3,7-dihydro-6-ethylamino-2-thio-2H-purin-2-one | 15.20 |
| 6-benzylamino-8-(cyclopropyl)-3,7-dihydro-3-propyl-2-thio-2H-purin-2-one hydrochloride | 33.60 |
| 8-cyclopropyl-3,7-dihydro-3-propyl-6-(4-pyridyl-methylamino)-2-thio-2H-purin-2-one | 0.41 |
| 6-cyclopentylamino-8-cyclopropyl-3,7-dihydro-3-propyl-2-thio-2H-purin-2-one hydrochloride | 7.41 |
| 6-butylamino-8-cyclopropyl-3,7-dihydro-3-propyl-2-thio-2H-purin-2-one | 24.48 |
| 8-cyclopropyl-3,7-dihydro-6-(2-hydroxyethylamino)-3-propyl-3-thio-2H-purin-2-one | 53.80 |
| 6-amino-8-cyclopropyl-3,7-dihydro-3-propyl-2-thio-2H-purin-2-one | 39.42 |
| 3-ethyl-6-cyclopentylamino-3,7-dihydro-8-isopropyl-2-thio-2H-purin-2-one | 9.40 |
| 6-cyclopentylamino-3,7-dihydro-8-isopropyl-3-propyl-2-thio-2H-purin-2-one | 45.10 |
| 3-ethyl-6-cyclopentylamino-8-cyclopropyl-3,7-dihydro-2-thio-2H-purin-2-one | 0.19 |
| 3-(4-chlorobenzyl)-6-cyclopentylamino-3,7-dihydro-8-isopropyl-2-thio-2H-purin-2-one | 114.50 |

EXAMPLE 12

Adenine Derivatives

Following the method of the above Examples, the following compounds were similarly prepared from the appropriate starting materials. All temperatures are in ° C. unless otherwise stated.

The data is provided in Table 3 below.

TABLE 3

ADENINES

| Compound | m.p. |
|---|---|
| 6-ethylamino-3-hexyl-3H-purine hydrochloride | 190–195 |
| 3-hexyl-6-methylamino-3H-purine | 142–3 |
| 8-cyclopropyl-6-ehtylamino-3-(3-methylbutyl)-3H-purine hydrochloride | 188–190 |
| 8-cyclopropyl-3-ethyl-6-propylamino-3H-purine hydrochloride | 186–188 |
| 8-cyclopropyl-3-ethyl-6-methylamino-3H-purine | 143–145 |
| 3-butyl-6-ethylamino-3H-purine | 127–129 |
| 3-butyl-8-cyclopropyl-6-ethylamino-3H-purine | 182–184 |
| 6-ethylamino-3-propyl-3H-purine | 157–159 |
| 8-cyclopropyl-6-ethylamino-3-propyl-3H-purine hydrochloride | 193–195 |
| 8-cyclopropyl-3-cyclopropylmethyl-6-ethylamino-3H-purine hydrochloride | 195–197 |
| 3-benzyl-6-ethylamino-3H-purine | 187–188 |
| 8-cyclopropyl-6-cyclopropylamino-3-propyl-3H-purine hydrochloride | 200–210 |
| 3-(2-methylbutyl)-6-(2-(piperazin-1-yl)ethylamino-3H-purine | 144–145 |
| 3-cyclohexylmethyl-6-ethylamino-3H-purine hydrochloride | 258–265 |
| 3-benzyl-6-ethylamino-8-(1-methylethyl)-3H-purine hydrochloride | 199–200 |
| 3-cyclohexylmethyl-8-cyclopropyl-6-ethylamino-3H-purine hydrochloride | 192–193 |
| 3-cyclopropylmethyl-8-isopropyl-6-ethylamino-3H-purine | 96–99 |
| 3-ethyl-8-isopropyl-6-benzylamino-3H-purine | 141–142 |
| 3-ethyl-8-isopropyl-6-ethylamino-3H-purine hydrochloride | 194–195 |
| 3-ethyl-8-cyclopentyl-6-benzylamino-3H-purine hydrochloride | 179–182 |
| 3-ethyl-8-cyclopentyl-6-ethylamino-3H-purine hydrochloride | 212–214 |
| 3-(4-chlorobenzyl)-6-ethylamino-3H-purine | |
| 3-(4-chlorobenzyl)-6-ethylamino-3H-purine hydrochloride | 251–4 |
| 3-(4-chlorobenzyl)-6-ethylamino-8-isopropyl-3H-purine | |
| 3-(4-chlorobenzyl)-6-ethylamino-8-isopropyl-3H-purine hydrochloride | 215–7 |
| 6-benzylamino-8-cyclopropyl-3-propyl-3H-purine | 153–55 |
| 8-cyclopropyl-6-hexylamino-3-propyl-3H-purine hydrochloride | 137–8 |
| 8-cyclopropyl-3-propyl-6-(4-pyridylmethylamino)-3H-purine dihydrochloride | 185–208 |
| 6-cyclopentylamino-8-cyclopropyl-3-propyl-3H-purine hydrochloride | 273–6 |
| 6-butylamino-8-cyclopropyl-3-propyl-3H-purine hydrochloride | 171–3 |
| 8-cyclopropyl-6-(2-hydroxyethylamino)-3-propyl-3H-purine | 217–9 |
| 6-(3-cyclopentyloxy-4-methoxybenzlamino)-8-cyclopropy-3-propyl-3H-purine hydrochoride | |
| 6-amino-8-cyclopropyl-3-propyl-3H-purine | 188–90 |
| 3-ethyl-6-cyclopentylamino-8-isopropyl-3H-purine hydrochloride | 183–4 |
| 6-cyclohexylamino-8-isopropyl-3-propyl-3H-purine hydrochloride | 202–3 |
| 6-cyclopentylamino-8-isopropyl-3-propyl-3H-purine hydrochloride | 207–10 |
| 3-ethyl-6-cyclopentylamino-8-cyclopropyl-3H-purine 3H-purine hydrochloride | 205–8 |
| 3-(4-chlorobenzyl)-6-cyclopentylamino-8-cyclopropyl-3H-purine hydrochloride | 269–73 |
| 6-cyclopentylamino-3-(3-cyclopentyloxy-4-methoxy-benzyl)-8-isopropyl-3H-purine hydrochloride | 193–5 |
| 3-(2-chlorobenzyl)-6-cyclopentylamino-8-isopropyl-3H-purine hydrochloride | 207–8 |
| 8-cyclopropyl-6-diethylamino-3-propyl-3H-purine hydrochloride | 173–9 |
| 8-cyclopropyl-6-(3-pentylamino-3-propyl-3H-purine hydrochloride | 187–9 |
| 6-ethylamino-8-isopropyl-3-(4-pyridylmethyl)-3H-purine dihydrochoride | 240–6 |

EXAMPLE 13

Elemental Analysis of Adenines

Elemental analysis was conducted for certain of the compounds set forth in the above tables. The results are provided below.

Elemental analysis for 8-cyclopropyl-3-ethyl-6-ethylamino-3H-purine hydrochloride 99%+1% ($H_2O$; HCl)

| | | | | |
|---|---|---|---|---|
| Calc. | C 53.29 | H 6.80 | N 25.90 | O 0.53 |
| Found | C 52.97 | H 7.01 | N 26.01 | O 0.34 |

Elemental analysis for 6-ethyl-amino-3-hexyl-3H-purine hydrochloride mp 188–94°

| | | | | |
|---|---|---|---|---|
| Calc. | C 55.02 | H 7.81 | N 24.68 | Cl 12.49 |
| Found | C 55.33 | H 8.05 | N 24.50 | Cl 12.71 |

Elemental analysis for 3-hexyl-6-methylamino-3H-purine hydrochloride mp 190–195°

| | | | | |
|---|---|---|---|---|
| Calc. | C 53.43 | H 7.47 | N 25.96 | Cl 13.14 |
| Found | C 53.70 | H 7.81 | N 25.92 | Cl 13.18 |

Elemental analysis for 8-cyclopropyl-6-ethyl-amino-3-(3-methylbutyl)-3H-purine hydrochloride

| | | | | |
|---|---|---|---|---|
| Calc. | C 58.15 | H 7.81 | N 22.60 | Cl 11.44 |
| Found | C 58.12 | H 8.01 | N 22.65 | Cl 11.46 |

Elemental analysis for 8-cyclopropyl-3-ethyl-6-propylamino-3H-purine hydrochloride

| | | | | |
|---|---|---|---|---|
| Calc. | C 55.41 | H 7.15 | N 24.85 | Cl 12.58 |
| Found | C 55.74 | H 7.06 | N 25.08 | Cl 12.71 |

Elemental analysis for 8-cyclo-propyl-3-ethyl-6-methylamino-3H-purine

| | | | |
|---|---|---|---|
| Calc. | C 60.81 | H 6.96 | N 32.23 |
| Found | C 60.58 | H 7.02 | N 32.67 |

Elemental analysis for 3-butyl-6-ethylamino-3H-purine hydrochloride mp 221–223°

| | | | | |
|---|---|---|---|---|
| Calc. | C 51.65 | H 7.09 | N 27.38 | Cl 13.88 |
| Found | C 51.74 | H 7.06 | N 27.62 | Cl 13.93 |

Elemental analysis for 3-butyl-8-cyclopropyl-6-ethylamino-3H-purine hydrochloride mp 194–196°

| | | | | |
|---|---|---|---|---|
| Calc. | C 56.83 | H 7.49 | N 23.67 | Cl 11.98 |
| Found | C 56.91 | H 6.98 | N 23.97 | Cl 12.03 |

Elemental analysis for 6-ethyl-amino3-propyl-3H-purine 98%+2% water

| | | | |
|---|---|---|---|
| Calc. | C 57.35 | H 7.44 | N 33.44 |
| Found | C 57.68 | H 7.22 | N 33.29 |

Elemental analysis for 8-cyclopropyl-6-ethylamnino-3-propyl-3H-purine hydrochloride

| | | | | |
|---|---|---|---|---|
| Calc. | C 55.41 | H 7.15 | N 24.85 | Cl 12.58 |
| Found | C 55.45 | H 7.13 | N 24.96 | Cl 12.71 |

Elemental analysis for 8-cyclopropyl-3-cyclopropylmethyl-6-ethylamino-3H-purine hydrochloride

| | | | | |
|---|---|---|---|---|
| Calc. | C 57.23 | H 6.87 | N 23.84 | Cl 12.07 |
| Found | C 57.49 | H 6.88 | N 23.59 | Cl 12.49 |

Elemental analysis for 3-benzyl-6-ethylamino-3H-purine

| | | | |
|---|---|---|---|
| Calc. | C 66.39 | H 5.97 | N 27.65 |
| Found | C 66.58 | H 5.63 | N 27.80 |

Elemental analysis for 8-cyclopropyl-6-cyclopropylamino-3-propyl-3H-purine hydrochloride

| | | | | |
|---|---|---|---|---|
| Calc. | C 57.23 | H 6.86 | N 23.84 | Cl 12.07 |
| Found | C 57.30 | H 6.90 | N 23.77 | Cl 12.16 |

Elemental analysis for 3-cyclohexylmethyl-6-ethylamimo-3H-purine hydrochloride

| | | | | |
|---|---|---|---|---|
| Calc. | C 56.84 | H 7.50 | N 23.67 | Cl 11.98 |
| Found | C 56.82 | H 7.54 | N 23.65 | Cl 12.05 |

Elemental analysis for 3-benzyl-6-ethylamino-8-(1-methylethyl)-3H-purine hydrochloride

| | | | | |
|---|---|---|---|---|
| Calc. | C 61.52 | H 6.68 | N 21.10 | Cl 10.68 |
| Found | C 61.52 | H 6.59 | N 21.18 | Cl 10.60 |

Elemental analysis for 3-cylohexylmethyl-8-cyclopropyl-6-ethylamino-3H-purine hydrochloride

| | | | | |
|---|---|---|---|---|
| Calc. | C 60.79 | H 7.80 | N 20.85 | Cl 10.56 |
| Found | C 60.55 | H 7.48 | N 20.85 | Cl 11.34 |

Elemental analysis for 3-cyclopropyl-methyl-8-isopropyl-6-ethylamino-3H-purine

| | | | |
|---|---|---|---|
| Calc. | C 64.84 | H 8.16 | N 27.00 |
| Found | C 64.42 | H 7.86 | N 26.87 |

Elemental analysis for 6-benzylamino-3-ethyl-8-isopropyl-6-ethylamino-3H-purine

| | | | |
|---|---|---|---|
| Calc. | C 69.12 | H 7.17 | N 23.71 |
| Found | C 69.27 | H 7.44 | N 23.60 |

Elemental analysis for 3-ethyl-8-isopropyl-6-ethylamino-3H-purine hydrochloride

| | | | |
|---|---|---|---|
| Calc. | C 53.43 | H 7.47 | N 25.96 |
| Found | C 53.62 | H 7.66 | N 25.34 |

Elemental analysis for 6-benzylamino-8-cyclopentyl-3-ethyl-3H-purine hydrochloride

| | | | |
|---|---|---|---|
| Calc. | C 63.78 | H 6.76 | N 19.57 |
| Found | C 63.55 | H 6.54 | N 19.51 |

Elemental analysis for 8-cyclopentyl-3-ethyl-6-ethylamino-3H-purine hydrochloride

| | | | |
|---|---|---|---|
| Calc. | C 56.84 | H 7.50 | N 23.67 |
| Found | C 56.54 | H 7.37 | N 23.63 |

EXAMPLE 14

PDE IV Inhibition by Adenine Compounds

The PDE IV inhibitory effect of certain of the compounds set forth above was examined according to the methods previously described. The results are provided in Table 4 below.

TABLE 4

PDE IV RESULTS

| Compound | calc PDE IV IC50 ($\mu$M) |
|---|---|
| 3-ethyl-8-isopropyl-6-ethylamino-3H-purine hydrochloride | 52.17 |
| 3-ethyl-8-cyclopentyl-6-benzylamino-3H-purine hydrochloride | 62.44 |
| 3-ethyl-8-cyclopentyl-6-ethylamino-3H-purine hydrochloride | 28.34 |
| 3-cyclohexylmethyl-6-ethylamino-3H-purine hydrochloride | 32.95 |
| 3-cyclohexylmethyl-8-cyclopropyl-6-ethylamino-3H-purine hydrochloride | 3.78 |
| 8-cyclopropyl-6-ethylamino-3-(3-methylbutyl)-3H-purine hydrochloride | 2.45 |
| 8-cyclopropyl-3-ethyl-6-propylamino-3H-purine hydrochloride | 15.67 |
| 3-hexyl-6-methylamino-3H-purine hydrochloride | 34.15 |
| 3-cyclopropylmethyl-8-isopropyl-6-ethylamino-3H-purine hydrochloride | 12.66 |
| 3-ethyl-8-isopropyl-6-benzylamino-3H-purine hydrochloride | 28.94 |
| 3-butyl-6-ethylamino-3H-purine hydrochloride | 66.41 |
| 3-butyl-8-cyclopropyl-6-ethylamino-3H-purine hydrochloride | 5.99 |
| 8-cyclopropyl-6-ethylamino-3-propyl-3H-purine hydrochloride | 6.31 |
| 3-(3-cyclopentyloxy-4-methoxybenzyl)-6-ethylamino-8-isopropyl-3H-purine hydrochloride | 0.32 |
| 3-(4-chlorobenzyl)-6-ethylamino-3H-purine hydrochloride | 37.75 |
| 3-ethyl-6-ethylamino-8-((3-cyclopentyloxy-4-methoxy)benzyl)-3H-purine hydrochloride | 4.52 |

EXAMPLE 15

Dithioxanthine derivatives of the present invention were manufactured and analyzed. The results are set forth in Table 5 below.

TABLE 5

DITHIOXANTHINES

| Compound | m.p. | IC50 PDE IV |
|---|---|---|
| 3,7-dihydro-3-ethyl-2,6-dithio-1H-purine-2,6-dione | 275–276 | |
| 3,7-dihydro-3-propyl-2,6-dithio-1H-purine-2,6-dione | 294–297 | |
| 3,7-dihydro-8-ethyl-3-dithio-2,6-dithio-1H-purine-2,6-dione | 266–267 | |
| 3-butyl-3,7-dihydro-2,6-dithio-1H-purine-2,6-dione | 249–251 | |
| 3-butyl-3,7-dihydro-8-ethyl-2,6-dithio-1H-purine-2,6-dione | 251–252 | |
| 3,7-dihydro-3,8-diethyl-2,6-dithio-1H-purine-2,6-dione | 260–261 | |
| 3-benzyl-3,7-dihydro-2,6-dithio-1H-purine-2,6-dione | 298–303 | 38.49 |
| 3,7-dihydro-3,8-hexyl-2,6-dithio-1H-purine-2,6-dione | 222–224 | |
| 8-cyclopropyl-3,7-dihydro-3-(3-methylbutyl)-2,6-dithio-1H-purine-2,6-dione | | 6.31 |
| 8-cyclopropyl-3,7-dihydro-3-ethyl-2,6-dithio-1H-purine-2,6-dione | | 6.18 |
| 3,7-dihydro-3-(2-methylbutyl)-2,6-dithio-1H-purine-2,6-dione | 263–4 | |
| 3-butyl-8-cyclopropyl-3,7-dihydro-2,6-dithio-1H-purine-2,6-dione | | 9.43 |
| 3-cyclopropylmethyl-3,7-dihydro-2,6-dithio-1H-purine-2,6-dione | 276–8 | |
| 8-cyclopropyl-3,7-dihydro-3-propyl-2,6-dithio-1H-purine-2,6-dione | | 64.49 |

TABLE 5-continued

DITHIOXANTHINES

| Compound | m.p. | IC50 PDE IV |
|---|---|---|
| 8-cyclopropyl-3-cyclopropylmethyl-3,7-dihydro-2,6-dithio-1H-purine-2,6-dione | | 2.27 |
| 3-butyl-3,7-dihydro-8-(1-methylethyl)-2,6-dithio-1H-purine-2,6-dione | | 5.93 |
| 3-cyclohexylmethyl-3,7-dihydro-2,6-dithio-1H-purine-2,6-dione | 292–4 | |
| 3-benzyl-3,7-dihydro-8-(1-methylethyl)-2,6-dithio-1H-purine-2,6-dione | | 3.40 |
| 3-cyclohexylmethyl-8-cyclopropyl-3,7-dihydro-2,6-dithio-1H-purine-2,6-dione | | 3.03 |
| 3-(3-cyclopentyloxy-4-methoxybenzyl)-3,7-dihydro-8-isopropyl-2,6-dithio-1H-purine-2,6-dione | 204–206 | 0.60 |
| 3-(3-cyclopentyloxy-4-methoxyoxybenzyl)-3,7-dihydro-2,6-dithio-1H-purine-2,6-dione | 204–206 | 0.60 |
| 3-(4-chlorobenzyl)-8-isopropyl)-3,7-dihydro-2,6-dithio-3,7-purine-2,6-dione | 242–243 | 2.40 |
| 3-ethyl-3,7-dihydro-8-isopropyl-2,6- | 248–250 | 4.10 |
| 3,7-dihydro-8-isopropyl-3-propyl-2,6-dithio-1H-purine-2,6-dione | 203 | 3.50 |
| 3-(2-chlorobenzyl)-3,7-dihydro-8-isopropyl-2,6-dithio-1H-purine-2,6-dione | 244–246 | 7.74 |
| 8-isopropyl-3-(4-pyridylmethyl)-2,6-dithio-1H-purine-2,6-dione | 310–315 | |

EXAMPLE 16

Pharmacological Tests

Isolated Guinea Pig Trachea

The test compound was dissolved in dimethylsulfoxide. Guinea pig isolated trachealis muscle was mounted in a bath containing Krebs solution maintained at 37.5° C. and bubbled with carbogen (95% $O_2$, 5% $CO_2$).

Tension changes were recorded isometrically using force displacement transducers in conjunction with potentiometric pen recorders.

The ability of the test compounds to relax airways muscle was investigated by the construction of cumulative concentration effect curves. Each concentration of the test compound was allowed to equilibrate with the tissue for 5 minutes before a concentration increment (ten-fold) was made.

In each tissue the test compound was compared with theophylline as standard.

| Compound | In Vitro Activity |
|---|---|
| Theophylline | 1 |
| 8-Cyclopropyl-3-ethyl-6-ethylamino-3H-purine | 43.7 |
| 6-Ethylamino-3-hexyl-3H-purine | 25.6 |
| 3-Benzyl-6-ethylamino-3H-purine | 18.5 |

EXAMPLE 17

In-Vivo Studies (i) The effect of test compounds in a model of bronchial hyperresponsiveness (BHR) and cellular infiltration in the guinea pig induced by ovalbumin (see, for example Morley et al, Agents and Actions, Supplement, 1988, 23, 187) were studied.

The test compound was administered at doses of 0.5 and 1.0 mg/kg/day given subcutaneously over 7 days by osmotic mini-pump. Theophylline and salbutamol at concentrations of 1 mg/kg/day were used as standards. Dose response curves to histamine (1–50 μg/kg) were constructed for each animal.

FIGS. 1–2 show the results obtained.

(ii) Sensitization and Challenge procedure: Male Dunkin Hartley guine pigs (Charles River) (200–250 g) were injected i.p. with ovalbumin (OVA) (0.5 ml/animal; 20 μg OVA in $Al(OH)_3$ (moist gel)); this preparation produced an injectable stable suspension containing excess $Al(OH)_3$. Sham animals were injected with 0.5 ml $Al(OH)_3$ alone. After a period of 18–21 days animals were exposed to an aerosol of OVA (100 μg/ml) for 1 hour in an exposure chamber.

(iii) Bronchoalveloar lavage: Animals were anesthetized, 24 hours after aerosol exposure, with urethane (25%, w/v, 7 ml/kg, i.p.) and the trachea cannulated. Bronchoalveolar lavage (BAL) was performed by instilling 5 ml sterile saline into the lungs via the tracheal cannula and the fluid was immediately removed. The fluid was reinjected and the procedure repeated 5 times in total. This procedure resulted in a 40–60% recovery of BAL fluid from the lungs of the guinea pig. Total cell counts were performed on the resultant BAL fluid using an unimproved Neubauer haemocytometer. Cytospin preparations were prepared using a Shandon Cytospin 2 centrifuge. Two drops of BAL fluid were added to each cytospin cup and the samples were centrifuged for 1 min at 1300 r.p.m. Slides were fixed in acetone and stained with haemotoxylin and carbol chromotrope according to the method described by Lendrum (Lendrum 1944), differential cell counts were performed on each slide by counting 200 cells at random, the cell types were classified as neutrophils, eosinophils and mononuclear cells according to standard morphological criteria. Cells were counted blind. The results are expressed as the number of neutrophils, eosinophils and mononuclear cells per ml of BAL fluid. The remaining BAL fluid was centrifuged (10 min., 1000 g) and the resultant cells and cell free supernatants were aliquotted and frozen for later assays. Compounds were solubilized in either DMSO or saline administered intraperitoreally at a dose of 5 mg/kg one hour prior to ovalbumin challenge. The results are provided below in Table 6.

TABLE 6

| Compound | N | Dose mg/kg ip | % Eosinophils in Bal x ± se | % Inhibition |
|---|---|---|---|---|
| DMSO Vehicle | 9 | — | 32 ± 6 | — |
| 3-(3-cyclopentyloxy-4-methoxybenzyl)-3,7-dihydro-8-isopropyl-2,6-dithio-1H-purin-2,6-dione | 6 | 5 | 17 ± 3 | 47% |
| Saline Vehicle | 14 | — | 33 ± 3 | — |
| 8-cyclopropyl-6-ethylamino-3-(3-methylbutyl)-3H-purine hydrochloride | 7 | 5 | 16 ± 4 | 52% |

TABLE 6-continued

| Compound | N | Dose mg/kg ip | % Eosinophils in Bal x ± se | % Inhibition |
|---|---|---|---|---|
| 3-(3-cyclopentyl-oxy-4-methoxy-benzyl)-6-ethylamino-8-isopropyl-3H-purine hydrochloride | 7 | 5 | 12 ± 2 | 64% |

EXAMPLE 18

Synthesis and Assay of Adenine Compounds

Following the previously set forth methods, the following adenine derivatives of the present invention were synthesized and assayed for PDE IV inhibition activity as provided in Table 7 below.

TABLE 7

PDE IV RESULTS

| Compound | calc PDE IV IC50 ($\mu$M) |
|---|---|
| 6-Amino-3-(3-cyclopentyloxy-4-methoxy-benzyl)-8-(1-methylethenyl)-3H-purine; | .091 |
| 6-Amino-8-benzyloxymethyl-3-(3-cyclopentyloxy-4-methoxy-benzyl)-3H-purine; | .052 |
| 6-amino-8-[(1-benzyloxy-1-methyl)ethyl]-3-[(3-cyclopentyloxy-4-methoxy)benzyl]-3H-purine; | .005 |
| 6-Amino-3-(3-cyclopentyloxy-4-methoxy-benzyl)-8-[1-(4-fluorobenzyloxy)-1-methyl-ethyl]-3H-purine; | .091 |
| [8-(1-benzyloxy-1-methyl)ethyl]3-[(3-cyclopentyloxy-4-methoxy)benzyl]-6-ethylamino-3H-purine; | .85 |
| 6-Amino-8-benzyloxymethyl-3-(3-cyclopentyloxy-4-methoxy-benzyl)-3H-purine; | .45 |
| 3-[(3-cyclopentyloxy-4-methoxy)benzyl]-6-ethylamino-8-[(1-hydroxy-1-methyl)ethyl]-3H-purine; | .85 |
| 6-Ethylamino-3-(3-butoxy-4-methoxy-benzyl)-8-isopropyl-3H-purine; | 1.4 |
| 6-amino-3-[(3-cyclopentyloxy-4-methoxy)benzyl]-8-[(1-hydroxy-1-methyl)ethyl]-3H-purine; | .25 |
| 3-[(3-cyclopentyloxy-4-methoxy)benzyl]-6-ethylamino-8-(1-methyl-ethyl)-3H-purine; | .27 |
| 6-ethylamino-2-(3,4-dimethoxybenzyl)-8-isopropyl-3H-purine; | .31 |
| 6-Amino-3-(3-cyclopentyloxy-4-methoxybenzyl)-3H-purine; | .31 |
| 3-(3-cyclopentyloxy-4-methoxybenzl)-6-dimethylamino-8-isopropyl-3H-purine; | 19.3 |
| 6-Ethylamino-3-[3-(3-hydroxycyclopentyloxy)-4-methoxybenzyl)]-8-(1-hydroxy-1-methylethyl)-3H-purine; | 2.6 |
| 6-ethylamino-3-(3-,4-methylenedioxybenzyl)-8-isopropyl-3H-purine; | .44 |
| 6-ethylamino-9-[(3-cyclopentyloxy-4-methoxy)benzyl]-8-isopropyl-3H-purine; | .66 |
| 3-(3-cyclopentyloxy-4-methoxybenzl)-6-amino-8-isopropyl 3H-purine; | .82 |
| 6-(amino-8-(1-benzyloxy-1-methylethyl-3-(3,4-dimethoxybenzyl)-3H-purine; | .94 |
| 3-(3-cyclopentyloxy-4-methoxybenzyl)-6-(3-cyclopentyloxy-4-methoxybenzylamino-8-isopropyl-3H-purine; | 1.14 |
| 6-ethylamino-8-isopropyl-3-(4-methoxybenzyl)-3H-purine; | 1.2 |
| 3-(3-((3-hydroxy)cyclopentyloxy)-4-methoxybenzyl)-6-ethylamino-8-isopropyl-3H-purine; | 1.36 |
| 3-(3-cyclopentyloxy-4-methoxybenzyl)-6-(N-benzoyl-N-ethylamino)-8-isopropyl-3H-purine; | 1.43 |
| 3-(4-chlorobenzyl)-6-cyclopropylamino-8-isopropyl-3H-purine; | 1.69 |
| 6-ethylamino-8-isopropyl-3-[(4-methyoxy-3-(4-hydroxybutoxy))benzyl]-3H-purine; | 1.75 |
| 6-ethylamino-3-(4-fluorobenzyl)-8-isopropyl-3H-purine; | 1.85 |
| 3-(3-chlorobenzyl)-6-ethylamino-8-isopropyl-3H-purine; | 2.15 |
| 3-[3-(3-Hydroxy-cyclopentyloxy)-4-methoxy-benzyl]-8-(1-hydroxy-1-methyl-ethyl)-3H-purine; | 2.25 |
| 3-[3-(3-hydroxy)cyclopentyloxy)]-4-methoxy)benzyl)-6-ehtylamino-8-isopropyl-3H-purine; | 2.28 |
| 6-amino-3-(3,4-dimethoxybenzyl)-8-isopropyl-3H-purine; | .92 |
| 6-Ethylamino-3-[3-cyclopentylmethoxy-4-methoxy-benzyl]-8-isopropyl-3H-purine; | 12.5 |
| 6-ethylamino-3-(3-hydroxy-4-methoxybenzyl)-8-isopropyl-3H-purine; | 2.73 |
| 6-Ethylamino-3-[3-(3,3-dimethylaminoethoxy-4-methoxy)]-8-isopropyl-3H-purine; | 8.95 |
| 3-[(3-cyclopentyloxy-4-methoxy)benzyl]-8-[(1-methyl-1-hydroxy)ethyl]-6-ethylamino-3H-purine; | 3.1 |
| 6-amino-3-[(3-benzyloxy-4-methoxy)benzyl]-8-[(1-benzyloxy-1-methyl)ethyl]-3H-purine; | 3.12 |
| 3-(3-cyclopentyloxy-4-methoxybenzyl)-6-((2,2,2-trifluoroethyl)amino)-8-isopropyl-3H-purine; | 12.8 |
| 6-Ethylamino-3-[3-(2,2,2)-azabicyclooctan-3-yloxy)-4-methoxy]-8-isopropyl-3H-purine; | 2.05 |
| 6-Ethylamino-3-[3-(1-methylpiperidin-4-yl-methoxy)-4-methoxy-benzy]-8-isopropyl-3H-purine; | 6.6 |
| 6-Amino-3-(3,4-dimethyoxybenzyl)-8-(1-methylethenyl)-3H-purine; | 3.7 |
| 6-amino-8-isopropyl-3-[(4-methoxy-3-([(4-hydroxybutoxy))benzyl]-3H-purine; | 4.2 |
| 3-{2-(4-chlorophenyl)-ethyl]-6-ethylamino-8-isopropyl-3H-purine; | 4.46 |
| 3-(4-chlorobenzyl)-6-((1-hydroxy)cyclopentylamino)-8-isopropyl-3H-purine; | 4.48 |
| 3-(4-chlorobenzyl)-6-cyclopentylamino-8-ispropyl-3H-purine; | 4.7 |
| 6-amino-3(3,4-methylenedixoybenzyl)-8-isopropyl-3H-purine; | 4.1 |
| 6-Ethylamino-3-[(exo-8-methyl-8-azabicyclo(3,2,1)-octan-3-yl-oxy)-4-methoxy-benzy]-8-isopropyl-3-H-purine; | 6.02 |
| 6-amino-3-((3-benzyloxy-4-methoxy)-bezyl)-8-isopropyl-3H-purine; | 6.4 |
| 3-(4-chlorophenyl)-6-ethylamino-8-isopropyl-3H-purine; | 6.5 |
| 6-ethylamino-3-[(3-hydroxy-4-methoxy)benzyl]-8-[(1-hydroxy-1-methyl)ethyl]-3H-purine; | 6.5 |
| 6-Ethylamino-3-[(3-pyridin-4-yl-methoxy)N-oxide-4-methoxy]-8-isopropyl-3H-purine; | 4.5 |
| 3-[3-Cyclohexanyl-4-oxy-4-methoxy-benzyl]-6-ethylamino-8-isopropyl-3H-purine; | 8.28 |
| 3-(4-chlorbenzyl)-2,6-di(ethylamino)-8-isopropyl-3H-purine; | 11.2 |
| 6-amino-3-(3-hydroxy-4-methoxy)-benzyl)-8-isopropyl-3H-purine; | 15.1 |
| 6-amino-3-[3-(4-hydroxybutoxy-4-methoxy)benzyl]-8-(1-hydroxy-1-methylethyl)-3H-purine hydrochloride; | 17.1 |
| 6-amino-3-(4-chlorobenzyl)-8-isopropyl-3H-purine; | 20.8 |
| 6-amino-3-cyclopentylmethyl-8-isopropyl-3H-purine; | 23.2 |
| 8-cyclopropyl-3-ethyl-6-ethylamino-3H-purine; | 27.1 |
| 6-Ethylamino-8-isopropyl-3-[3-(pyridin-4-yl-methoxy)-4-methoxy-benzyl]-3H-purine; | 24.5 |
| 6-Ethylamino-3-(1-oxopyridin-4-yl-methyl)-8-isopropyl-3H-purine; and | 385 |
| 6-amino-3-[(3-hydroxy-4-methoxy)benzyl)]]-8-[(1-hydroxy-1-methyl)ethyl]-3H-purine. | 71000 |

While the invention has been illustrated with respect to the production and use of a particular compound, it is apparent that variations and modifications of the invention can be made without departing from the spirit or scope of the invention.

What is claimed is:

1. A compound of the formula (II):

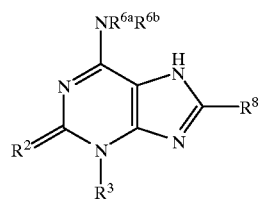

wherein $R_2$ is O or S;

$R_{6a}$ represents H a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_3$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_8$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_3$ or $C_{7-8}$ monocyclic cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and pharmaceutically acceptable salts thereof.

2. The compound of claim 1, wherein $R_3$ represents a $C_{1-8}$ alkyl, $C_{3-7}$ cycloalkyl, $C_{4-8}$ cycloalkylalkyl, aryl or ar($C_{1-4}$) alkyl group; $R_{6a}$ represents a $C_{1-8}$ alkyl, $C_{3-7}$ cycloalkyl, $C_{4-8}$ cycloalkylalkyl, aryl ar($C_{1-4}$)alkyl group, or heterocyclyl ($C_{1-4}$) alkyl group; $R_{6b}$ represents a hydrogen atom or a $C_{1-8}$ alkyl, $C_{3-7}$ cycloalkyl, $C_{4-8}$ cycloalkylalkyl, aryl or ar($C_{1-4}$)alkyl group; or —$NR_{6a}R_{6b}$ together forms a 5-membered or 6-membered ring, which ring optionally contains one or more additional heteroatoms; and $R_8$ represents a $C_{1-8}$ alkyl, $C_{3-7}$ cycloalkyl, $C_{4-8}$ cycloalkylalkyl, aryl, ar($C_{1-4}$)alkyl, pyridyl or pyridyl($C_{1-4}$)alkyl group.

3. The compound of claim 2, wherein $R_3$ represents a $C_{1-8}$ alkyl group, an ar($C_{1-4}$) alkyl group, or a $C_{3-7}$ cycloalkyl group.

4. The compound of claim 2, wherein $R_{6a}$ represents a $C_{1-8}$ alkyl group and $R_{6b}$ represents a hydrogen atom.

5. The compound of claim 2, wherein $R_8$ represents a $C_3$ or $C_7$ cycloalkyl group.

6. The compound of claim 5, wherein $R_8$ represents a cyclopropyl group.

7. The compound of claim 2, wherein $R_8$ represents a $C_{1-8}$ alkyl group.

8. The compound of claim 7, wherein $R_8$ represents an isopropyl group.

9. The compound of claim 3, wherein $R_3$ represents a $C_{1-4}$ alkyl group.

10. The compound of claim 2, wherein $R_{6a}$ represents methyl or ethyl and $R_{6b}$ represents a hydrogen atom.

11. The compound of claim 2, wherein $R_3$ represents propyl.

12. The compound of claim 2, wherein $R_3$ represents substituted or unsubstituted benzyl.

13. The compound of claim 2, wherein $R_3$ represents cyclopropylmethyl.

14. A compound selected from the group consisting of 8-cyclopropyl-3,7-dihydro-3-propyl-6(4-pyridylmethylamino)-2-thio-2H-purin-2-one; 6-cyclopentylamino-8-cyclopropyl-3,7-dihydro-3-propyl-2- thio-2H-purin-2-one; 8-cyclopropyl-3,7-dihydro-6-(2-hydroxyethylamino)-3-propyl-2-thio-2H-purin-2-one; 3-benzyl-3,7-dihydro-6-methylamino-2-thio-2H-purin-2-one; 3-butyl-3,7-dihydro-6-ethylamino-2-thio-2H-purin-2-one; 6-ethylamino-3,7-dihydro-3-propyl-2-thio-2H-purin-2-one; 3-benzyl-6-ethylamino-3,7-dihydro-2-thio-2H-purin-2-one; 3-((2-methyl)butyl))-6-(2-(piperazine-1-yl)ethylamino)-3,7-dihydro-2-thio-2H-purin-2-one; 3-cyclohexylmethyl-3,7-dihydro-6-ethylamino-2-thio-2H-purin-2-one; and their pharmaceutically acceptable salts.

15. A compound selected from the group consisting of: 3,8-diethyl-3,7-dihydro-6-morpholino-2H-2-thio-purin-2-one;

3-(cyclopropylmethyl)-3,7-dihydro-8-isopropyl-6-propylamino-2-thio-2H-purin-2-one;

3,7-dihydro-6-ethylamino-3-hexyl-2-thio-2H-purin-2-one;

3,7-Dihydro-3-hexyl-6-methylamino-2-thio-2H-purin-2-one;

8-cyclopropyl-3,7-dihydro-6-ethylamino-3-(3-methylbutyl)-2-thio-2H-purin-2-one;

8-cyclopropyl-3,7-dihydro-3-ethyl-6-propylamino-2-thio-2H-purin-2-one;

3-butyl-8-cyclopropyl-3,7-dihydro-6-ethylamino-2-thio-2H-purin-2-one;

6-ethylamino-3,7-dihydro-3-propyl-2-thio-2H-purin-2-one;

8-cyclopropyl-6-ethylamino-3,7-dihydro-3-propyl-2-thio-2H-purin-2-one;

8-cyclopropyl-3-cyclopropylmethyl-6-ethylamino-3,7-dihydro-2-thio-2H-purin-2-one;

3-benzyl-6-ethylamino-3,7-dihydro-2-thio-2H-purin-2-one;

8-cyclopropyl-6-cyclopropylamino-3-propyl-3,7-dihydro-2-thio-2H-purin-2-one hydrochloride;

3-((2-methyl)butyl))-6-(2-(piperazine-1-yl)ethylamino)-3,7-dihydro-2-thio-2H-purin-2-one;

3-cyclohexylmethyl-3,7-dihydro-6-ethylamino-2-thio-2H-purin-2-one;

3-benzyl-6-ethylamino-3,7-dihydro-8-(1-methylethyl)-2-thio-2H-purin-2-one;

3-cyclohexylmethyl-8-cyclopropyl-3,7-dihydro-6-ethylamino-2-thio-2H-purin-2-one;

6-benzylamino-8-(cyclopropyl)-3,7-dihydro-3-(propyl)-2-thio-2H-purin-2-one hydrochloride;

8-(cyclopropyl)-3,7-dihydro-6-hexylamino-3-(propyl)-2-thio-2H-purin-2-one hydrochloride;

6-butylamino-8-cyclopropyl-3,7-dihydro-3-propyl-2-thio-2H-purine-2-one;

6-cyclopropyl-3,7-dihydro-6-(2-hydroxyethylamino)-2-thio-2H-purine-2-one;

6-amino-8-cyclopropyl-3,7-dihydro-3-propyl-2-thio-2H-purine-2-one;

6-cyclopentylamino-3-ethyl-3,7-dihydro-8-isopropyl-2-thio-2H-purine-2-one;

6-cyclohexylamino-3,7-dihydro-8-isopropyl-3-propyl-2-thio-2H-purine-2-one;

6-cyclopentylamino-3,7-dihydro-8-isopropyl-3-propyl-2-thio-2H-purine-2-one;

6-cyclopentylamino-3-ethyl-8-cyclopropyl-3,7-dihydro-2-thio-2H-purine-2-one;

3-(4-chlorobenzyl)-6-cyclopentylamino-3,7-dihydro-8-isopropyl-2-thio-2H-purine-2-one;

6-cyclopentylamino-3-(3-cyclopentyl-4-methoxybenzyl)-3,7-dihydro-8-isopropyl-2-thio-2H-purine-2-one;

3-(2-chlorobenzyl)-6-cyclopentylamino-3,7-dihydro-8-isopropyl-2-thio-purine-2-one;

8-cyclopropyl-3,7-dihydro-6-(3-pentyl)-3-propyl-2-thio-2H-purin-2-one;

6-ethyl-8-isopropyl-3,7-dihydro-3-(4-pyridylmethyl, -2-thio-2H-purin-2-one;

3-(cyclopropylmethyl)-3,7-dihydro-8-( 1-methyl-ethyl)-6-propylamino-2-thio-2H-purin-2-one hydrochloride;

8-cyclopropyl-3-ethyl-6-ethylamino-3,7-dihydro-2-thio-2H-purin-2-one;

8-cyclopropyl-3,7-dihydro-3-propyl-6-(4-pyridylmethylamino)-2-thio-2H-purin-2-one;

6-cyclopentylamino-8-cyclopropyl-3,7-dihydro-3-propyl-2-thio-2H-purin-2-one hydrochloride;

3-ethyl-6-cyclopentylamino-3,7-dihydro-8-isopropyl-2-thio-2H-purin-2-one;

3-ethyl-6-cyclopentylamino-8-cyclopropyl-3,7-dihydro-2-thio-2H-purin-2-one; and their pharmaceutically acceptable salts.

16. A compound of the formula (II):

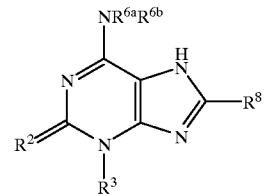

(II)

wherein $R_2$ is O or S;

$R_{6a}$ represents H a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_3$, represents a $C_{4-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1–C_3$ alkyl, nitro, trifluoromethyl, $C_1–C_6$ alkoxy or $C_3–C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1–C_4$) wherein said heterocyclyl moiety is a five to seven membered ring having at least one carbon atom and up to three nitrogen atoms, up to two oxygen atoms, and up to two sulfur atoms;

$R_8$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1–C_8$ alkylamido, $C_1–C_3$ dialkylamido, OH, $C_{1-6}$ alkoxy, $C_{3-6}$ cycloalkoxy, CH=NOH, CH=NOCONH$_2$, $C_1–C_3$ alkyl, phenyl or benzyl; aralkyl ($C_{1-4}$), optionally substituted with halogen, $C_1–C_3$ alkyl, nitro, trifluoromethyl, $C_1–C_6$ alkoxy or $C_3–C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1–C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and where the heterocyclyl is optionally substitutable as in aryl on the carbons or nitrogens of that ring; or a pharmaceutically acceptable salt thereof.

17. A compound of the formula (II):

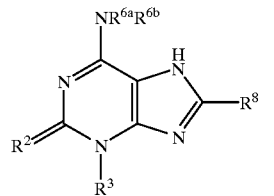

(II)

wherein $R_2$ is O or S;

$R_{6a}$ represents H a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1–C_8$ alkylamido, $C_1–C_3$ dialkylamido, OH, $C_{1-6}$ alkoxy, $C_{3-6}$ cycloalkoxy, CH=NOH, CH=NOCONH$_2$, $C_1–C_3$ alkyl, phenyl or benzyl; aralkyl ($C_{1-4}$), optionally substituted with halogen, $C_1–C_3$ alkyl, nitro, trifluoromethyl, $C_1–C_6$ alkoxy or $C_3–C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1–C_4$) wherein said heterocyclyl moiety is a five to seven membered ring having at least one carbon atom and up to three nitrogen atoms, up to two oxygen atoms, and up to two sulfur atoms;

$R_3$, represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1–C_8$ alkylamido, $C_1–C_3$ dialkylamido, OH, $C_{1-6}$ alkoxy, $C_{3-6}$ cycloalkoxy, CH=NOH, CH=NOCONH$_2$, $C_1–C_3$ alkyl, phenyl or benzyl; aralkyl ($C_{1-4}$), optionally substituted with halogen, $C_1–C_3$ alkyl, nitro, trifluoromethyl, $C_1–C_6$ alkoxy or $C_3–C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1–C_4$) wherein said heterocyclyl moiety is a five to seven membered ring having at least one carbon atom and up to three nitrogen atoms, up to two oxygen atoms, and up to two sulfur atoms;

$R_8$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{6-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1–C_8$ alkylamido, $C_1–C_3$ dialkylamido, OH, $C_{1-6}$ alkoxy, $C_{3-6}$ cycloalkoxy, CH=NOH, CH=NOCONH$_2$, $C_1–C_3$ alkyl, phenyl or benzyl; aralkyl ($C_{1-4}$), optionally substituted with halogen, $C_1–C_3$ alkyl, nitro, trifluoromethyl, $C_1–C_6$ alkoxy or $C_3–C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1–C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and where the heterocyclyl is optionally substitutable as in aryl on the carbons or nitrogens of that ring; or a pharmaceutically acceptable salt thereof.

18. A compound of the formula (II):

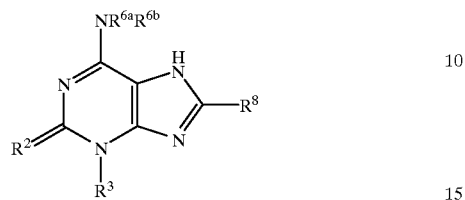

(II)

wherein $R_2$ is O or S;

$R_{6a}$ represents H a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_3$ represents a $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_8$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and pharmaceutically acceptable salts thereof.

19. A compound of the formula (II):

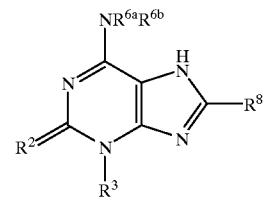

(II)

wherein $R_2$ is O or S;

$R_{6a}$ represents H a $C_{1-8}$ alkyl which is unbranched or branched and unsubstituted or substituted with $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_3$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_8$ represents a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and pharmaceutically acceptable salts thereof.

20. A pharmaceutical composition comprising a pharmaceutically acceptable carrier and a compound of the formula (II):

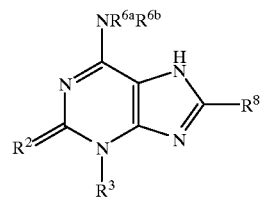

wherein $R_2$ is O or S;

$R_3$, $R_{6a}$ and $R_8$ are the same or different and each represents H or a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_4$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, NH$_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms, up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =NOCONH$_2$, =O; and pharmaceutically acceptable salts thereof.

21. The composition of claim 20, wherein $R_3$ represents a $C_{1-8}$ alkyl, $C_{3-7}$ cycloalkyl, $C_{4-8}$ cycloalkylalkyl, aryl or ar($C_{1-4}$)alkyl group; $R_{6a}$ represents a $C_{1-8}$ alkyl, $C_{3-7}$ cycloalkyl, $C_{4-8}$ cycloalkylalkyl, aryl ar($C_{1-4}$)alkyl group, or heterocyclyl ($C_{1-4}$) alkyl group; $R_{6b}$ represents a hydrogen atom or a $C_{1-8}$ alkyl, $C_{3-7}$ cycloalkyl, $C_{4-8}$ cycloalkylalkyl, aryl or ar($C_{1-4}$)alkyl group; or —NR$_{6a}$R$_{6b}$ together forms a 5-membered or 6-membered ring, which ring optionally contains one or more additional heteroatoms; and $R_8$ represents a $C_{1-8}$ alkyl, $C_{3-7}$ cycloalkyl, $C_{4-8}$ cycloalkylalkyl, aryl, ar($C_{1-4}$)alkyl, pyridyl or pyridyl($C_{1-4}$)alkyl group.

22. The composition of claim 21, wherein $R_3$ represents a $C_{1-8}$ alkyl group, an ar($C_{1-4}$) alkyl group, or a $C_{3-7}$ cycloalkyl group.

23. The composition of claim 21, wherein $R_{6a}$ represents a $C_{1-8}$ alkyl group and $R_{6b}$ represents a hydrogen atom.

24. The composition of claim 21, wherein $R_8$ represents a $C_{3-7}$ cycloalkyl group.

25. The composition of claim 24, wherein $R_8$ represents a cyclopropyl group.

26. The composition of claim 21, wherein $R_8$ represents a $C_{1-8}$ alkyl group.

27. The composition of claim 26, wherein $R_8$ represents an isopropyl group.

28. The composition of claim 22, wherein $R_3$ represents a $C_{1-4}$ alkyl group.

29. The composition of claim 21, wherein $R_{6a}$ represents methyl or ethyl and $R_{6b}$ represents a hydrogen atom.

30. The composition of claim 21, wherein $R_3$ represents propyl.

31. The composition of claim 21, wherein $R_3$ represents substituted or unsubstituted benzyl.

32. The composition of claim 21, wherein $R_3$ represents cyclopropylmethyl.

33. A pharmaceutical composition comprising a pharmaceutically acceptable carrier and a compound selected from the group consisting of 8-cyclopropyl-3,7-dihydro-3-propyl-6(4-pyridylmethylamino)-2-thio-2H-purin-2-one; 6-cyclopentylamino-8-cyclopropyl-3,7-dihydro-3-propyl-2-thio-2H-purin-2-one; 8-cyclopropyl-3,7-dihydro-6-(2-hydroxyethylamino)-3-propyl-2-thio-2H-purin-2-one; 3-benzyl-3,7-dihydro-6-methylamino-2-thio-2H-purin-2-one; 3-butyl-3,7-dihydro-6-ethylamino-2-thio-2H-purin-2-one; 6-ethylamino-3,7-dihydro-3-propyl-2-thio-2H-purin-2-one; 3-benzyl-6-ethylamino-3,7-dihydro-2-thio-2H-purin-2-one; 3-((2-methyl)butyl))-6-(2-(piperazine-1-yl)ethylamino)-3,7-dihydro-2-thio-2H-purin-2-one; 3-cyclohexylmethyl-3,7-dihydro-6-ethylamino-2-thio-2H-purin-2-one; and their pharmaceutically acceptable salts.

34. The composition of claim 20, wherein the compound is selected from the group consisting of 3,8-diethyl-3,7-dihydro-6-morpholino-2H-2-thio-purin-2-one;

3-(cyclopropylmethyl)-3,7-dihydro-8-isopropyl-6-propylamino-2-thio-2H-purin-2-one;

3,7-dihydro-6-ethylamino-3-hexyl-2-thio-2H-purin-2-one;

3,7-Dihydro-3-hexyl-6-methylamino-2-thio-2H-purin-2-one;

8-cyclopropyl-3,7-dihydro-6-ethylamino-3-(3-methylbutyl)-2-thio-2H-purin-2-one;

8-cyclopropyl-3,7-dihydro-3-ethyl-6-propylamino-2-thio-2H-purin-2-one;

3-butyl-8-cyclopropyl-3,7-dihydro-6-ethylamino-2-thio-2H-purin-2-one;

6-ethylamino-3,7-dihydro-3-propyl-2-thio-2H-purin-2-one;

8-cyclopropyl-6-ethylamino-3,7-dihydro-3-propyl-2-thio-2H-purin-2-one;

8-cyclopropyl-3-cyclopropylmethyl-6-ethylamino-3,7-dihydro-2-thio-2H-purin-2-one;

3-benzyl-6-ethylamino-3,7-dihydro-2-thio-2H-purin-2-one;

8-cyclopropyl-6-cyclopropylamino-3-propyl-3,7-dihydro-2-thio-2H-purin-2-one hydrochloride;

3-((2-methyl)butyl))-6-(2-piperazine-1-yl)ethylamino)-3,7-dihydro-2-thio-2H-purin-2-one;

3-cyclohexylmethyl-3,7-dihydro-6-ethylamino-2-thio-2H-purin-2-one;

3-benzyl-6-ethylamino-3,7-dihydro-8-(1-methylethyl)-2-thio-2H-purin-2-one;

3-cyclohexylmethyl-8-cyclopropyl-3,7-dihydro-6-ethylamino-2-thio-2H-purin-2-one;

6-benzylamino-8-(cyclopropyl)-3,7-dihydro-3-(propyl)-2-thio-2H-purin-2-one hydrochloride;

8-(cyclopropyl)-3,7-dihydro-6-hexylamino-3-(propyl)-2-thio-2H-purin-2-one hydrochloride;

6-butylamino-8-cyclopropyl-3,7-dihydro-3-propyl-2-thio-2H-purine-2-one;

6-cyclopropyl-3,7-dihydro-6-(2-hydroxyethylamino)-2-thio-2H-purine-2-one;

6-amino-8-cyclopropyl-3,7-dihydro-3-propyl-2-thio-2H-purine-2-one;

6-cyclopentylamino-3-ethyl-3,7-dihydro-8-isopropyl-2-thio-2H-purine-2-one;

6-cyclohexylamino-3,7-dihydro-8-isopropyl-3-propyl-2-thio-2H-purine-2-one;

6-cyclopentylamino-3,7-dihydro-8-isopropyl-3-propyl-2-thio-2H-purine-2-one;

6-cyclopentylamino-3-ethyl-8-cyclopropyl-3,7-dihydro-2-thio-2H -purine-2-one;

3-(4-chlorobenzyl)-6-cyclopentylamino-3,7-dihydro-8-isopropyl-2-thio-2H-purine-2-one;

6-cyclopentylamino-3-(3-cyclopentyl-4-methoxybenzyl)-3,7-dihydro-8-isopropyl-2-thio-2H-purine-2-one;

3-(2-chlorobenzyl)-6-cyclopentylamino-3,7-dihydro-8-isopropyl-2-thio-purine-2-one;

8-cyclopropyl-3,7-dihydro-6-(3-pentyl)-3-propyl-2-thio-2H-purin-2-one;

6-ethyl-8-isopropyl-3,7-dihydro-3-(4-pyridylmethyl)-2-thio-2H-purin-2-one;

3-(cyclopropylmethyl)-3,7-dihydro-8-(1-methyl-ethyl)-6-propylamino -2-thio-2H-purin-2-one hydrochloride;

8-cyclopropyl-3-ethyl-6-ethylamino-3,7-dihydro-2-thio-2H-purin-2-one;

8-cyclopropyl-3,7-dihydro-3-propyl-6-(4-pyridylmethylamino)-2-thio-2H-purin-2-one;

6-cyclopentylamino-8-cyclopropyl-3,7-dihydro-3-propyl-2-thio-2H-purin-2-one hydrochloride;

3-ethyl-6-cyclopentylamino-3,7-dihydro-8-isopropyl-2-thio-2H-purin-2-one;

3-ethyl-6-cyclopentylamino-8-cyclopropyl-3,7-dihydro-2-thio-2H-purin-2-one; and their pharmaceutically acceptable salts.

35. A method of treating a mammal suffering from a disease state selected from the group consisting of asthma, allergies, inflammation, depression, atopic diseases, and rhinitis, comprising administering to the mammal an effective amount of a compound of the formula (II):

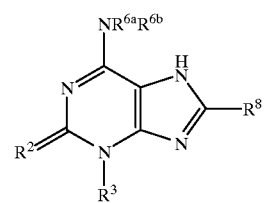

wherein $R_2$ is O or S;

$R_3$, $R_{6a}$ and $R_8$ are the same or different and each represents H or a $C_{1-8}$ alkyl which is unbranched or branched and unsubstituted or substituted with OH, $C_{1-6}$ alkoxy, $C_{3-6}$ cycloalkoxy, $CO_2H$, =NOH, =NOCONH$_2$, or =O; $C_{3-8}$ cycloalkyl which is unsubstituted or substituted with OH, $C_{1-6}$ alkoxy, $C_{3-6}$ cycloalkoxy, halogen, haloalkyl, $CO_2H$, =NOH, =NOCONH$_2$, or =O; $C_{4-8}$ cycloalkylalkyl wherein the cycloalkyl portion is unsubstituted or substituted with OH, $C_{1-6}$ alkoxy, $C_{3-6}$ cycloalkoxy, $CO_2H$, =NOH, =NOCONH$_2$, or =O; aryl which is unsubstituted or substituted with Cl, $NH_2$, alkylamino, dialkylamino, amido, $C_1$–$C_8$ alkylamido, $C_1$–$C_3$ dialkylamido, OH, $C_{1-6}$ alkoxy, $C_{3-6}$ cycloalkoxy, CH=NOH, CH=NOCONH$_2$, $C_1$–$C_3$ alkyl, phenyl or benzyl; aralkyl ($C_{1-4}$), optionally substituted with halogen, $C_1$–$C_3$ alkyl, nitro, trifluoromethyl, $C_1$–$C_6$ alkoxy or $C_3$–$C_6$ cycloalkoxy; a five to seven membered heterocyclyl ring having at least one carbon atom and up to three nitrogen atoms, up to two oxygen atoms, and up to two sulfur atoms; and heterocyclylalkyl ($C_1$–$C_4$) wherein said heterocyclyl moiety is a five to seven membered ring having at least one carbon atom and up to three nitrogen atoms up to two oxygen atoms, and up to two sulfur atoms;

$R_{6b}$ represents a H or $R_{6a}$, or together $R_{6b}$, N, and $R_{6a}$ make a 3 to 8 member ring containing at least one carbon atom, from one to three nitrogen atoms, from zero to two oxygen atoms, from zero to two sulfur atoms, said ring optionally substituted with alkoxy, $CO_2H$, $CONH_2$, =NOH, =$NOCONH_2$, =O; and pharmaceutically acceptable salts thereof.

36. The method of claim 35, wherein $R_3$ represents a $C_{1-8}$ alkyl, $C_{3-7}$ cycloalkyl, $C_{4-8}$ cycloalkylalkyl, aryl or ar($C_{1-4}$) alkyl group; $R_{6a}$ represents a $C_{1-8}$ alkyl, $C_{3-7}$ cycloalkyl, $C_{4-8}$ cycloalkylalkyl, aryl ar($C_{1-4}$)alkyl group, or heterocyclyl ($C_{1-4}$) alkyl group; $R_{6b}$ represents a hydrogen atom or a $C_{1-8}$ alkyl, $C_{3-7}$ cycloalkyl, $C_{4-8}$ cycloalkylalkyl, aryl or ar($C_{1-4}$)alkyl group; or —$NR_{6a}R_{6b}$ together forms a 5-membered or 6-membered ring, which ring optionally contains one or more additional heteroatoms; and $R_8$ represents a $C_{1-8}$ alkyl, $C_{3-7}$ cycloalkyl, $C_{4-8}$ cycloalkylalkyl, aryl, ar($C_{1-4}$)alkyl, pyridyl or pyridyl($C_{1-4}$)alkyl group.

37. The method of claim 36, wherein $R_3$ represents a $C_{1-8}$ alkyl group, an ar($C_{1-4}$) alkyl group, or a $C_{3-7}$ cycloalkyl group.

38. The method of claim 36, wherein $R_{6a}$ represents a $C_{1-8}$ alkyl group and $R_{6b}$ represents a hydrogen atom.

39. The method of claim 36, wherein $R_8$ represents a $C_{3-7}$ cycloalkyl group.

40. The method of claim 36, wherein $R_8$ represents a cyclopropyl group.

41. The method of claim 36, wherein $R_8$ represents a $C_{1-8}$ alkyl group.

42. The method of claim 41, wherein $R_8$ represents an isopropyl group.

43. The method of claim 37, wherein $R_3$ represents a $C_{1-4}$ alkyl group.

44. The method of claim 36, wherein $R_{6a}$ represents methyl or ethyl and $R_{6b}$ represents a hydrogen atom.

45. The method of claim 36, wherein $R_3$ represents propyl.

46. The method of claim 36, wherein $R_3$ represents substituted or unsubstituted benzyl.

47. The method of claim 36, wherein $R_3$ represents cyclopropylmethyl.

48. The method of claim 31, wherein the compound is selected from the group consisting of 8-cyclopropyl-3,7-dihydro-3-propyl-6(4-pyridylmethylamino)-2-thio-2H-purin-2-one; 6-cyclopentylamino-8-cyclopropyl-3,7-dihydro-3-propyl-2-thio-2H-purin-2-one; 8-cyclopropyl-3,7-dihydro-6-(2-hydroxyethylamino)-3-propyl-2-thio-2H-purin-2-one; and their pharmaceutically acceptable salts.

49. The method of claim 31, wherein the compound is selected from the group consisting of:
3,8-diethyl-3,7-dihydro-6-morpholino-2H-2-thio-purin-2-one;
3-(cyclopropylmethyl)-3,7-dihydro-8-isopropyl-6-propylamino-2-thio-2H-purin-2-one;
3,7-dihydro-6-ethylamino-3-hexyl-2-thio-2H-purin-2-one;
3,7-Dihydro-3-hexyl-6-methylamino-2-thio-2H-purin-2-one;
3-benzyl-3,7-dihydro-6-methylamino-2-thio-2H-purin-2-one;
8-cyclopropyl-3,7-dihydro-6-ethylamino-3-(3-methylbutyl)-2-thio-2H-purin-2-one;
8-cyclopropyl-3,7-dihydro-3-ethyl-6-propylamino-2-thio-2H-purin-2-one;
3-butyl-3,7-dihydro-6-ethylamino-2-thio-2H-purin-2-one;
3-butyl-8-cyclopropyl-3,7-dihydro-6-ethylamino-2-thio-2H-purin-2-one;
6-ethylamino-3,7-dihydro-3-propyl-2-thio-2H-purin-2-one;
8-cyclopropyl-6-ethylamino-3,7-dihydro-3-propyl-2-thio-2H-purin-2-one;
8-cyclopropyl-3-cyclopropylmethyl-6-ethylamino-3,7-dihydro-2-thio-2H-purin-2-one;
3-benzyl-6-ethylamino-3,7-dihydro-2-thio-2H-purin-2-one;
8-cyclopropyl-6-cyclopropylamino-3-propyl-3,7-dihydro-2-thio-2H-purin-2-one hydrochloride;
3-((2-methyl)butyl))-6-(2-(piperazine-1-yl)ethylamino)-3,7-dihydro-2-thio-2H-purin-2-one;
3-cyclohexylmethyl-3,7-dihydro-6-ethylamino-2-thio-2H-purin-2-one;
3-benzyl-6-ethylamino-3,7-dihydro-8-(1-methylethyl)-2-thio-2H-purin-2-one;
3-cyclohexylmethyl-8-cyclopropyl-3,7-dihydro-6-ethylamino-2-thio-2H-purin-2-one;
6-benzylamino-8-(cyclopropyl)-3,7-dihydro-3-(propyl)-2-thio-2H-purin-2-one hydrochloride;
8-(cyclopropyl)-3,7-dihydro-6-hexylamino-3-(propyl)-2-thio-2H-purin-2-one hydrochloride;
6-butylamino-8-cyclopropyl-3,7-dihydro-3-propyl-2-thio-2H-purine-2-one;
6-cyclopropyl-3,7-dihydro-6-(2-hydroxyethylamino)-2-thio-2H-purine-2-one;
6-amino-8-cyclopropyl-3,7-dihydro-3-propyl-2-thio-2H-purine-2-one;
6-cyclopentylamino-3-ethyl-3,7-dihydro-8-isopropyl-2-thio-2H-purine-2-one;
6-cyclohexylamino-3,7-dihydro-8-isopropyl-3-propyl-2-thio-2H-purine-2-one;
6-cyclopentylamino-3,7-dihydro-8-isopropyl-3-propyl-2-thio-2H-purine-2-one;
6-cyclopentylamino-3-ethyl-8-cyclopropyl-3,7-dihydro-2-thio-2H-purine-2-one;
3-(4-chlorobenzyl)-6-cyclopentylamino-3,7-dihydro-8-isopropyl-2-thio-2H-purine-2-one;
6-cyclopentylamino-3-(3-cyclopentyl-4-methoxybenzyl)-3,7-dihydro-8-isopropyl-2-thio-2H-purine-2-one;
3-(2-chlorobenzyl)-6-cyclopentylamino-3,7-dihydro-8-isopropyl-2-thio-purine-2-one;
8-cyclopropyl-3,7-dihydro-6-(3-pentyl)-3-propyl-2-thio-2H-purin-2-one;
6-ethyl-8-isopropyl-3,7-dihydro-3-(4-pyridylmethyl)-2-thio-2H-purin-2-one;
3-(cyclopropylmethyl)-3,7-dihydro-8-(1-methyl-ethyl)-6-propylamino-2-thio-2H-purin-2-one hydrochloride;
8-cyclopropyl-3-ethyl-6-ethylamino-3,7-dihydro-2-thio-2H-purin-2-one;
8-cyclopropyl-3,7-dihydro-3-propyl-6-(4-pyridylmethylamino)-2-thio-2H-purin-2-one;
6-cyclopentylamino-8-cyclopropyl-3,7-dihydro-3-propyl-2-thio-2H-purin-2-one hydrochloride;
3-ethyl-6-cyclopentylamino-3,7-dihydro-8-isopropyl-2-thio-2H-purin-2-one;
3-ethyl-6-cyclopentylamino-8-cyclopropyl-3,7-dihydro-2-thio-2H-purin-2-one; and their pharmaceutically acceptable salts.

50. The method of claim 31, wherein $R_8$ represents a hydrogen.

* * * * *